United States Patent
Barbero et al.

(10) Patent No.: US 11,467,161 B2
(45) Date of Patent: Oct. 11, 2022

(54) BIOMARKERS OF THERAPEUTIC RESPONSIVENESS

(71) Applicant: Meso Scale Technologies, LLC., Rockville, MD (US)

(72) Inventors: Simone Barbero, Germantown, MD (US); Eli N. Glezer, Del Mar, CA (US); Anu Mathew, North Potomac, MD (US); Mingyue Wang, Potomac, MD (US)

(73) Assignee: Meso Scale Technologies, LLC., Rockville, MD (US)

(*) Notice: Subject to any disclaimer, the term of this patent is extended or adjusted under 35 U.S.C. 154(b) by 0 days.

(21) Appl. No.: 15/386,346

(22) Filed: Dec. 21, 2016

(65) Prior Publication Data

US 2017/0205418 A1 Jul. 20, 2017

Related U.S. Application Data

(62) Division of application No. 14/169,308, filed on Jan. 31, 2014, now abandoned.

(60) Provisional application No. 61/759,437, filed on Feb. 1, 2013.

(51) Int. Cl.
```
G01N 33/574    (2006.01)
A61K 31/44     (2006.01)
A61K 31/404    (2006.01)
C12Q 1/48      (2006.01)
```

(52) U.S. Cl.
CPC ..... *G01N 33/57438* (2013.01); *A61K 31/404* (2013.01); *A61K 31/44* (2013.01); *C12Q 1/485* (2013.01); *G01N 33/5743* (2013.01); *G01N 2800/60* (2013.01)

(58) Field of Classification Search
None
See application file for complete search history.

(56) References Cited

U.S. PATENT DOCUMENTS

| | | |
|---|---|---|
| 4,168,146 A | 9/1979 | Grubb et al. |
| 4,235,601 A | 11/1980 | Deutsch et al. |
| 4,366,241 A | 12/1982 | Tom et al. |
| 4,442,204 A | 4/1984 | Greenquist et al. |
| 5,208,535 A | 5/1993 | Nakayama et al. |
| 5,807,522 A | 9/1998 | Brown et al. |
| 6,110,426 A | 8/2000 | Shalon et al. |
| 7,842,246 B2 | 11/2010 | Wohlstadter et al. |
| 2003/0113713 A1 | 6/2003 | Glezer et al. |
| 2003/0207290 A1 | 11/2003 | Kenten et al. |
| 2004/0022677 A1 | 2/2004 | Wohlstadter et al. |
| 2004/0189311 A1 | 9/2004 | Glezer et al. |
| 2005/0052646 A1 | 3/2005 | Wohlstadter et al. |
| 2005/0142033 A1 | 6/2005 | Glezer et al. |
| 2006/0205012 A1 | 9/2006 | Debad et al. |
| 2009/0148859 A1* | 6/2009 | Liotta .............. G01N 33/6842 435/7.1 |
| 2014/0141985 A1 | 5/2014 | Glezer et al. |
| 2014/0309263 A1 | 10/2014 | Barbero et al. |

FOREIGN PATENT DOCUMENTS

| | | |
|---|---|---|
| WO | 99/26067 A1 | 5/1999 |
| WO | 2004/058055 A2 | 7/2004 |
| WO | 2007/040559 A2 | 4/2007 |
| WO | 2010/127057 A2 | 11/2010 |
| WO | WO 2010/127057 | * 11/2010 |

OTHER PUBLICATIONS

Cho et al (Clinical Genitourinary Cancer, 2007, 5:379-385).*
Jonasch et al (Cancer, 2010, 116:57-65).*
Tsavachidou-Fenner et al, Annals of Oncology; 2010, 21:1599-1606.*
Mollica et al (Cancers, 2019, 11:830; 16 pages).*
Tamaskar et al (Clinical Advances in Hematology & Oncology, 2011, 9:101-110).*
Van der Mijn et al (Drug Resistance Updates, 2014, 17:77-88).*
Nandagopal et al (Expert Opinion on Investigational Drugs, 2019, 28:10, 851-860).*
Shojael et al (Cancer Research, 2010, 70:10090-100).*
Marona et al (Cells, 2019, 8: 272, internet pp. 1-17).*
Gamez-Pozo et al (Neoplasia, 2012, 14:1144-1152).*
Morris et al (Oncogene, 2010, 29:2104-2117).*
Sivanand et al (Science Translational Medicine, 2012, 4:137ra75, internet pp. 1-17).*
Bachelder R.E. et al., "Vascular Endothelial Growth Factor is an Autocrine Survival Factor for Neuropilin-Expressing Breast Carcinoma Cells", Cancer Research 61(15):15736-5740 (Aug. 1, 2001).
Berns A., "Gene Expression in Diagnosis", Cancer 403:491-492 (2000).
Chang Y.S. et al., "Sofafenib (BAY 43-9006) Inhibits Tumor Growth and Vascularization and Induces Tumor Apoptosis and Hypoxia in RCC Xenograft Models", Cancer Chemother Pharmacol 59(5):561-574 (2007).
Chen R. et al., "Simultaneous Quantification of Six Human Cytokines in a Single Sample Using Microparticle-Based Flow Cytometric Technology", Clinical Chemistry 45(9):1693-1694 (1999).
Chen Z. et al., "Crucial Role of p53-Dependent Cellular Senescence in Suppression of Pten-Deficient Tumorigenesis", Nature 436:725-730 (Aug. 4, 2005).
Delehanty J.B., "Printing Functional Protein Microarrays Using Piezoelectric Capillaries", Methods in Molecular Biology 264:135-143 (2004).
Fan Y. et al., "An Antisense Oligodeoxynucleotide to p21Waf1/Cip1 Causes Apoptosis in Human Breast Cancer Cells", Molecular Cancer Therapeutics 2(8):773-782 (Aug. 2003).

(Continued)

*Primary Examiner* — Laura B Goddard
(74) *Attorney, Agent, or Firm* — Scully, Scott, Murphy & Presser, P.C.

(57) ABSTRACT

The present invention relates to methods of diagnosing a kidney disorder in a patient, as well as methods of monitoring the progression of a kidney disorder and/or methods of monitoring a treatment protocol of a therapeutic agent or a therapeutic regimen. The invention also relates to assay methods used in connection with the diagnostic methods described herein.

13 Claims, 10 Drawing Sheets

(56) References Cited

OTHER PUBLICATIONS

Garcia J.A. et al., "Recent Progress in the Management of Advanced Renal Cell Carcinoma", CA A Cancer Journal for Clinicians 57(2):112-125 (2007).

Horiguchi A. et al., "Elevated AKT Activation and its Impact on Clinicopathological Features of Renal Cell Carcinoma", The Journal of Urology 169(2):710-713 (Feb. 2003).

Jung J.E. et al., "STAT3 is Potential Modulator of HIF-1-Mediated VEGF Expression in Human Renal Carcinoma Cells", The FASEB Journal 19(10), pp. 1-18 (2005).

Kummar S. et al., "Compressing Drug Development Timelines in Oncology Using Phase '0' Trials", Nature Reviews Cancer 7(2):131-139 (Feb. 2007).

Lee T-H et al., "Vascular Endothelial Growth Factor Mediates Intracrine Survival in Human Breast Carcinoma Cells Through Internally Expressed VEGFR1/FLT1", PloS Medicine 4(6):1101-1116 (Jun. 2007).

Li Y. et al., "AKT/PKB Phosphorylation of p21Cip/WAF1 Enhances Protein Stability of p21Cip/WAF1 and Promotes Cell Survival", The Journal of Biological Chemistry 277(13):11352-11361 (Mar. 29, 2002).

Lovett R.A., "Toxicogenomics: Toxicologists Brace for Genomics Revolution", Science 289(5479):536-537 (2000).

Lue R.Y.P. et al., "Site-Specific Immobilization of Biotinylated Proteins for Protein Microarray Analysis", Methods in Molecular Biology 264:85-100 (2004).

Masood R. et al., "Vascular Endothelial Growth Factor (VEGF) in an Autocrine Growth Factor for VEGF Receptor-Positive Human Tumors", Blood 98(6):1904-1913 (Sep. 15, 2001).

Miyata Y. et al., "Presence of Phosphorylated Hepatocyte Growth Factor Receptor/c-Met is Associated with Tumor Progression and Survival in Patients with Conventional Renal Cell Carcinoma", Clin Cancer Research 12(16):4876-4881 (Aug. 15, 2006).

Motoshima H. et al., "AMPK and Cell Proliferation-AMPK as a Therapeutic Target for Atherosclerosis and Cancer", J Physiol 574.1:63-71 (2006).

Murphy D.A. et al., "Inhibition of Tumor Endothelial ERK Activation, Angiogenesis, and Tumor Growth by Sorafenib (BAY43-9006)", The American Journal of Pathology 169(5):1875-1885 (Nov. 2006).

Nagata D. et al., "AMP-Activated Protein Kinase (AMPK) Signaling in Endothelial Cells is Essential for Angiogenesis in Response to Hypoxic Stress", The Journal of Biological Chemistry 278(33):31000-31006 (Aug. 2003).

Oberoi P. et al., "Conjugated Antibody Characterization is Critical for Reducing Variability in Immunogenicity and Biomarker Assays", American Assoc. Pharmaceutical Scientists Annual Meeting 2012, Post M1072) (1 page).

Panka D.J. et al., "GSK-3 Inhibition Enhances Sorafenib-Induced Apoptosis in Melanoma Cell Lines", The Journal of Biological Chemistry 283(2):726-732 (Jan. 11, 2008).

Park M.K. et al., "A Latex Bead-Based Flow Cytometric Immunoassay Capable of Simultaneous Typing of Multiple Pneumococcal Serotypes (Multibead Assay)", Clinical and Diagnostic Laboratory Immunology 7(3):486-489 (2000).

Rini B.I., "Vascular Endothelial Growth Factor-Targeted Therapy in Renal Cell Carcinoma: Current Status and Future Directions", Clin Cancer Research 13(4):1098-1106 (Feb. 15, 2007).

Skates S.J. et al., "Pooling of Case Specimens to Create Standard Serum Sets for Screening Cancer Biomarkers", Cancer Epidemiol Biomarkers Prev. 16(2):334-341 (2007).

Vignali D.A.A., "Multiplexed Particle-Based Flow Cytometric Assays", Journal of Immunological Methods 243:243-255 (2000).

Walt D.R., "Molecular Biology: Bead-Based Fiber-Optic Arrays", Science 287(5452):451-452 (2000).

Waltenberger J. et al., "Different Signal Transduction Properties of KDR and Flt1, Two Receptors for Vascular Endothelial Growth Factor", The Journal of Biological Chemistry 269(43):26988-26995 (Oct. 1994).

Weiss R.H., "p21Waf1/Cip1 as a Therapeutic Target in Breast and Other Cancers", Cancer Cell 4(6):425-429 (Dec. 2003).

Weiss R.H. et al., "p21 is a Prognostic Marker for Renal Cell Carcinoma: Implications for Novel Therapeutic Approaches", The Journal of Urology 177(1):63-69 (Jan. 2007).

Wilhelm S.M. et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis", Cancer Research 64(19):7099-7109 (Oct. 1, 2004).

Zare M. et al., "Growth Factors, Signal Transduction Pathways, and Tumor Suppressor Genes in Esophageal Cancer", Esophageal Cancer-Cell and Molecular Biology, Biomarkers, Nutrition and Treatment, prof. Ferdous Rasetgar (Ed.), ISBN:978-953-51-0223-6, InTech) (29 pages) (2012).

Meso Scale Discovery® Toxicology Applications (Oct. 2011) (24 pages).

MSD® Multi-Spot Assay System, Akt Signaling Panel Whole Cell Lysate Kit (21 pages) (Jun. 2011).

Meso Scale Discovery® Assays and Kits (4 pages) (Mar. 2011).

U.S. Office Action dated Jun. 29, 2016 received in U.S. Appl. No. 14/169,308.

U.S. Final Office Action dated Nov. 9, 2015 received in U.S. Appl. No. 14/169,308.

U.S. Office Action dated Mar. 18, 2015 received in U.S. Appl. No. 14/169,308.

\* cited by examiner

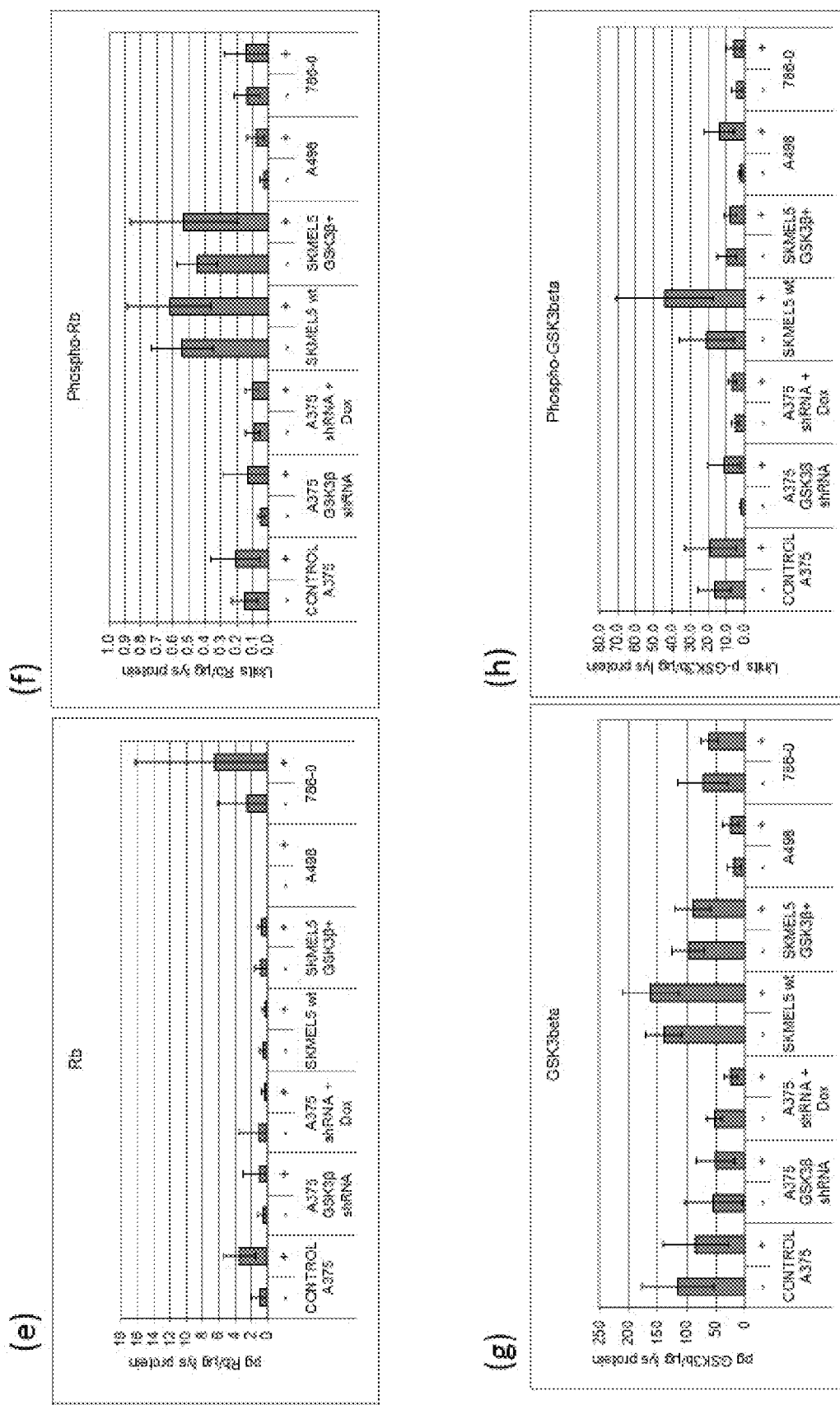
Fig. 1(e)-(h)

BIOMARKERS OF THERAPEUTIC RESPONSIVENESS

CROSS REFERENCE TO RELATED APPLICATIONS

The present application is a divisional of co-pending application having U.S. Ser. No. 14/169,308, filed on Jan. 31, 2014, which claims benefit of U.S. Provisional Application No. 61/759,437 filed on Feb. 1, 2013, the entire contents of which are incorporated herein by reference.

STATEMENT REGARDING FEDERALLY-SPONSORED RESEARCH

This invention was made with federal support under HHSN261201000104C awarded by the National Cancer Institute. The U.S. government has certain rights in the invention.

FIELD OF THE INVENTION

This application relates to assay methods useful in the detection and treatment of renal cell carcinoma (RCC) and/or metastatic melanoma.

BACKGROUND OF THE INVENTION

Challenges in the field of oncology include the lack of efficient means for early cancer detection and for specific cancer subtyping and for measuring and/or predicting responsiveness to therapy. There is a need for new cancer biomarkers that can provide early and specific diagnosis of cancer and enable targeted therapy and prognosis. The need for new diagnostics has been the impetus behind many initiatives targeting the discovery and development of new biomarkers for cancer. The hope is that the identification of suitable biomarkers will allow for the development of early cancer detection screening tests and will lead to improved cancer therapy and a reduction in the mortality associated with many cancers.

Kinases are specialized proteins that function within intracellular communication networks known as signal transduction pathways. Preclinical studies have shown that these pathways are important in the development of tumor vasculature and in the proliferation of tumor cells, leading to tumor growth and metastases. Therefore, by blocking the kinases involved in these signaling pathways, tumor growth and proliferation may be controlled. Kinases are located on multiple levels of signaling pathways. Receptor tyrosine kinases are located upstream in the signaling pathway of tumor vasculature (e.g., VEGFR and PDGFR) and tumor cells (e.g., Kit and FLT-3). Serine/threonine kinases are located downstream in the signaling pathway within the cells of tumors and tumor vasculature (e.g., RAF/MEK/ERK).

ynthase kinase-3, GSK3, isoforms GSK-3α and GSK-3β, are constitutively active serine/threonine protein kinases involved in the regulation of WNT signaling (wingless pathway) (beta-catenin); initiation of protein translation (elF2B); glycogen synthesis (glycogen synthase, GS); promotion of mitochondrial apoptosis (Bax) and other signaling elements such as cyclin D1, heat shock factor-1 (HSF-1), c-jun and p53. GSK3 is involved in the regulation of a wide range of additional cell factors and responses.

Active GSK-3β promotes beta-catenin degradation and inhibits protein synthesis. Beta-catenin is the penultimate downstream mediator of WNT signaling. In the nucleus it interacts as a coactivator with lymphoid enhancer factor/T cell factor (Lef/Tcf) transcription factors. GSK-3β phosphorylates and promotes the betaTrCP (beta-Transducin repeat containing protein) targeted ubiquitin-proteosome pathway degradation of beta-catenin inhibits protein synthesis by phosphorylating elF2Bepsilon, a subunit of elF2B.

The degradation of beta-catenin and inhibition of protein synthesis are suppressed by the phosphorylation of GSK-3β. GSK-3β is phosphorylated by a number of kinases. Among these are Akt/PKB and MAPKAP-K1 (aka RSK-2; p90rsk) which are activated by a PI3K-PDK-PKB(Akt) and Ras-Raf-MEK-MAPK (ERK1, ERK 2, ERK 3 and ERK-5)-RSK2 pathways, respectively.

SUMMARY OF THE INVENTION

The invention provides a method for evaluating the efficacy of a treatment regimen in a patient diagnosed with renal cell carcinoma (RCC) or metastatic melanoma, said method comprising
(a) obtaining a test sample from a patient undergoing said treatment regimen for RCC;
(b) measuring a level of a biomarker in said test sample, wherein said biomarker comprises total, phosphorylated, and dephosphorylated isoforms of c-Met, beta-catenin, SFRP-1, Akt, Wnt3A, Rb, VEGF, E-cadherin, GSK3beta, and combinations thereof;
(c) comparing said level to a normal control level of said biomarker; and
(d) evaluating from said comparing step (c) whether said patient is responsive to said treatment regimen.

The invention further provides a method for evaluating the efficacy of a treatment regimen in a patient diagnosed with renal cell carcinoma (RCC) or metastatic melanoma, said method comprising
(a) ordering a test comprising a measurement of a level of a biomarker in a test sample obtained from a patient undergoing said treatment regimen for RCC, wherein said biomarker comprises total, phosphorylated, and dephosphorylated isoforms of c-Met, beta-catenin, SFRP-1, Akt, Wnt3A, Rb, VEGF, E-cadherin, GSK3beta, and combinations thereof;
(b) comparing said level to a normal control level of said biomarker; and
(c) evaluating from said comparing step (b) whether said patient is responsive to said treatment regimen.

Another embodiment is a method of administering a treatment regimen to a patient in need thereof for treating renal cell carcinoma (RCC) or metastatic melanoma, comprising:
(a) obtaining a test sample from a patient undergoing said treatment regimen for RCC;
(b) measuring a level of a biomarker in said test sample, wherein said biomarker comprises total, phosphorylated, and dephosphorylated isoforms of c-Met, beta-catenin, SFRP-1, Akt, Wnt3A, Rb, VEGF, E-cadherin, GSK3beta, and combinations thereof;
(c) comparing said level to a normal control level of said biomarker;
(d) evaluating from said comparing step (c) whether said patient is responsive to said treatment regimen; and
(e) adjusting said treatment regimen based on said evaluating step (d).

A further embodiment is a method of administering a treatment regimen to a patient in need thereof for treating renal cell carcinoma (RCC) or metastatic melanoma, comprising:

(a) obtaining a test sample from a patient prior to the commencement of said treatment regimen for RCC;

(b) measuring a level of a biomarker in said test sample, wherein said biomarker comprises total, phosphorylated, and dephosphorylated isoforms of c-Met, beta-catenin, SFRP-1, Akt, Wnt3A, Rb, VEGF, E-cadherin, GSK3beta, and combinations thereof;

(c) comparing said level to a normal control level of said biomarker;

(d) evaluating from said comparing step (c) whether said patient will be responsive to said treatment regimen; and (e) administering said treatment regimen based on said evaluating step (d).

The invention also contemplates a method of administering a treatment regimen to a patient in need thereof for treating renal cell carcinoma (RCC) or metastatic melanoma, comprising:

(a) evaluating a level of a biomarker in a test sample obtained from a patient undergoing said treatment regimen for RCC or metastatic melanoma relative to a normal control level of said biomarker, wherein said biomarker comprises total, phosphorylated, and dephosphorylated isoforms of c-Met, beta-catenin, SFRP-1, Akt, Wnt3A, Rb, VEGF, E-cadherin, GSK3beta, and combinations thereof; and (b) adjusting said treatment regimen based on said evaluating step (a).

Still further, the invention includes a method of administering a treatment regimen to a patient in need thereof for treating renal cell carcinoma (RCC) or metastatic melanoma, comprising:

(a) evaluating a level of a biomarker in a test sample obtained from a patient prior to the commencement of said treatment regimen for RCC or metastatic melanoma relative to a normal control level of said biomarker, wherein said biomarker comprises total, phosphorylated, and dephosphorylated isoforms of c-Met, beta-catenin, SFRP-1, Akt, Wnt3A, Rb, VEGF, E-cadherin, GSK3beta, and combinations thereof; and (b) administering said treatment regimen based on said evaluating step (a).

Additionally, the invention contemplates a method of treating renal cell carcinoma (RCC) or metastatic melanoma, comprising administering a VEGF-inhibitor to a patient whose levels of a biomarker for RCC or metastatic melanoma were determined to be at least 1.5-fold greater/less than those values in a normal control, wherein said biomarker of RCC or metastatic melanoma is selected from total, phosphorylated, and dephosphorylated isoforms of c-Met, beta-catenin, SFRP-1, Akt, Wnt3A, Rb, VEGF, E-cadherin, and GSK3beta.

Moreover, the invention includes a method for detecting abnormal GSK3beta activity in a patient diagnosed with renal cell carcinoma (RCC) or metastatic melanoma, said method comprising (a) obtaining a test sample from said patient;

(b) measuring a level of a biomarker in said test sample, wherein said biomarker comprises total, phosphorylated, and dephosphorylated isoforms of c-Met, beta-catenin, SFRP-1, Akt, Wnt3A, Rb, VEGF, E-cadherin, GSK3beta, and combinations thereof;

(c) comparing said level to a normal control level of said biomarker; and (d) evaluating from said comparing step (c) whether said GSK3beta activity is abnormal relative to said normal control level of said biomarker.

Also provided is a method for detecting an alteration in GSK3beta activity in a patient diagnosed with renal cell carcinoma (RCC) or metastatic melanoma, said method comprising (a) obtaining a baseline test sample from said patient at $t_0$;

(b) measuring a baseline level of a biomarker in said baseline test sample, wherein said biomarker comprises total, phosphorylated, and dephosphorylated isoforms of c-Met, beta-catenin, SFRP-1, Akt, Wnt3A, Rb, VEGF, E-cadherin, GSK3beta, and combinations thereof;

(c) obtaining an additional test sample from said patient at time $t_{(0+n)}$, wherein n is >1 hour from $t_0$;

(d) measuring an additional level of said biomarker in said additional test sample;

(e) comparing said additional level to said baseline level of said biomarker; and (f) evaluating from said comparing step (e) whether said GSK3beta activity is altered relative to said baseline level of said biomarker.

Another embodiment of the invention is a kit for the analysis of a kidney disease panel comprising (a) a multi-well assay plate comprising a plurality of wells, each well comprising at least four discrete binding domains to which capture antibodies to the following human analytes are bound: c-Met, beta-catenin, SFRP-1, Akt, Wnt3A, Rb, VEGF, GSK3beta, and combinations thereof;

(b) in one or more vials, containers, or compartments, a set of labeled detection antibodies specific for said human analytes; and (c) in one or more vials, containers, or compartments, a set of calibrator proteins.

DETAILED DESCRIPTION OF THE INVENTION

Figure 1A:
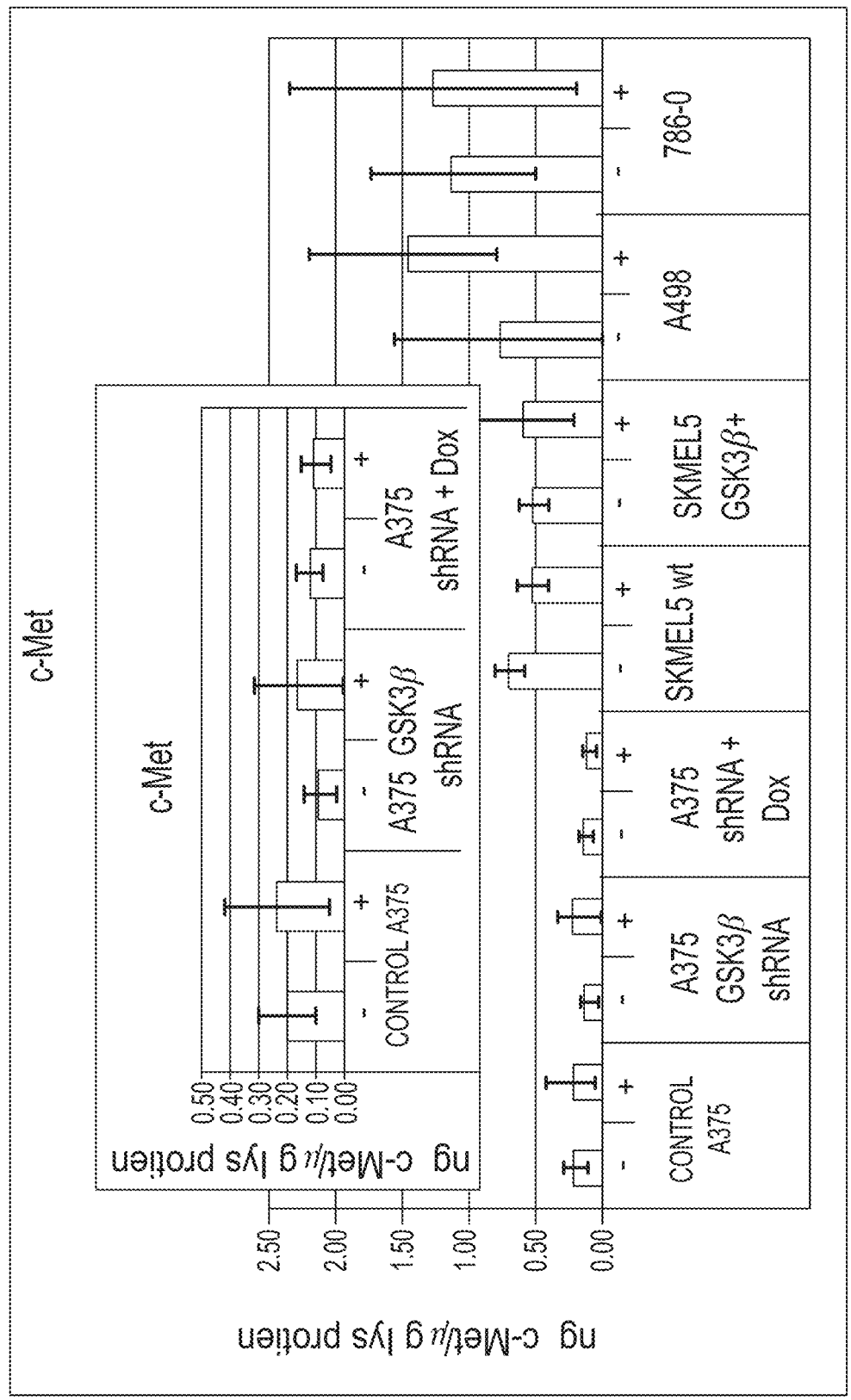
FIG. 1(a)-(n) show the levels of individual markers in tumor sample sets 1, 2, and 3 measured on MSD panels. Samples that were not treated with drug are designated as (−) and those treated with drug as (+). The A375 and SKMEL5 tumor-bearing mice were treated with sorafenib, and the A498 and 786-0 tumor-bearing mice treated with sunitinib.
Figure 1B:
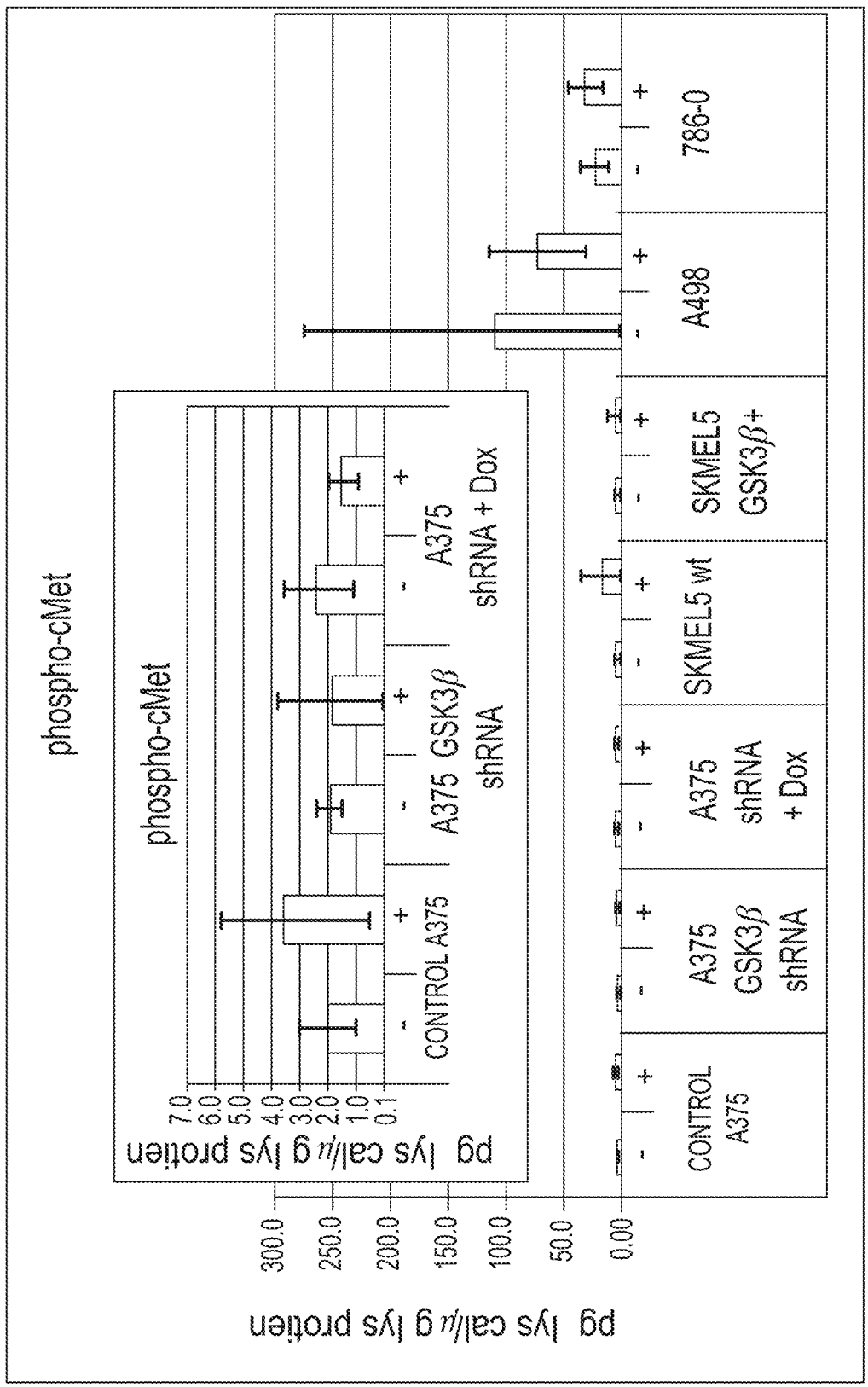
Figure 1C:
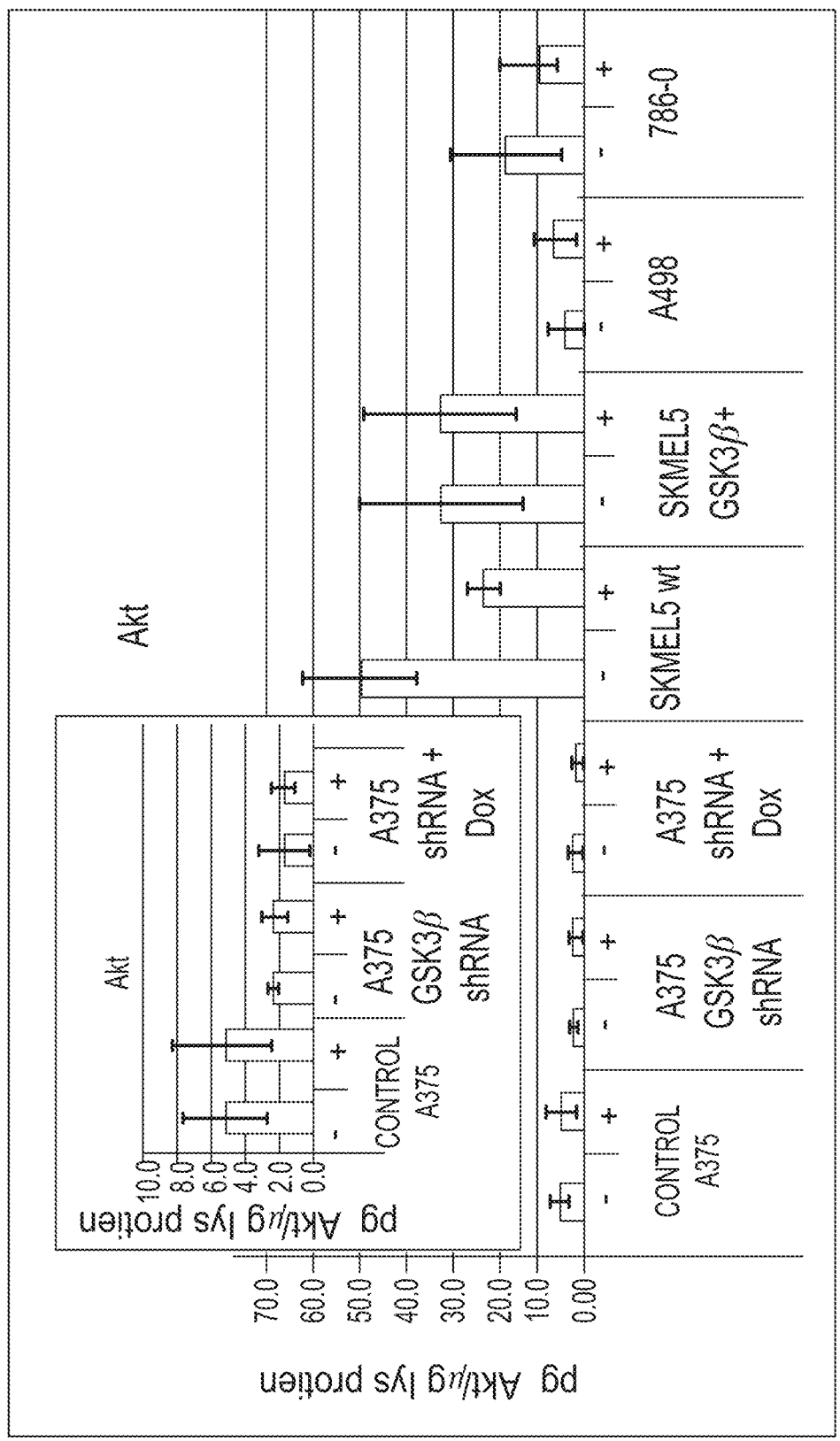
Figure 1D:
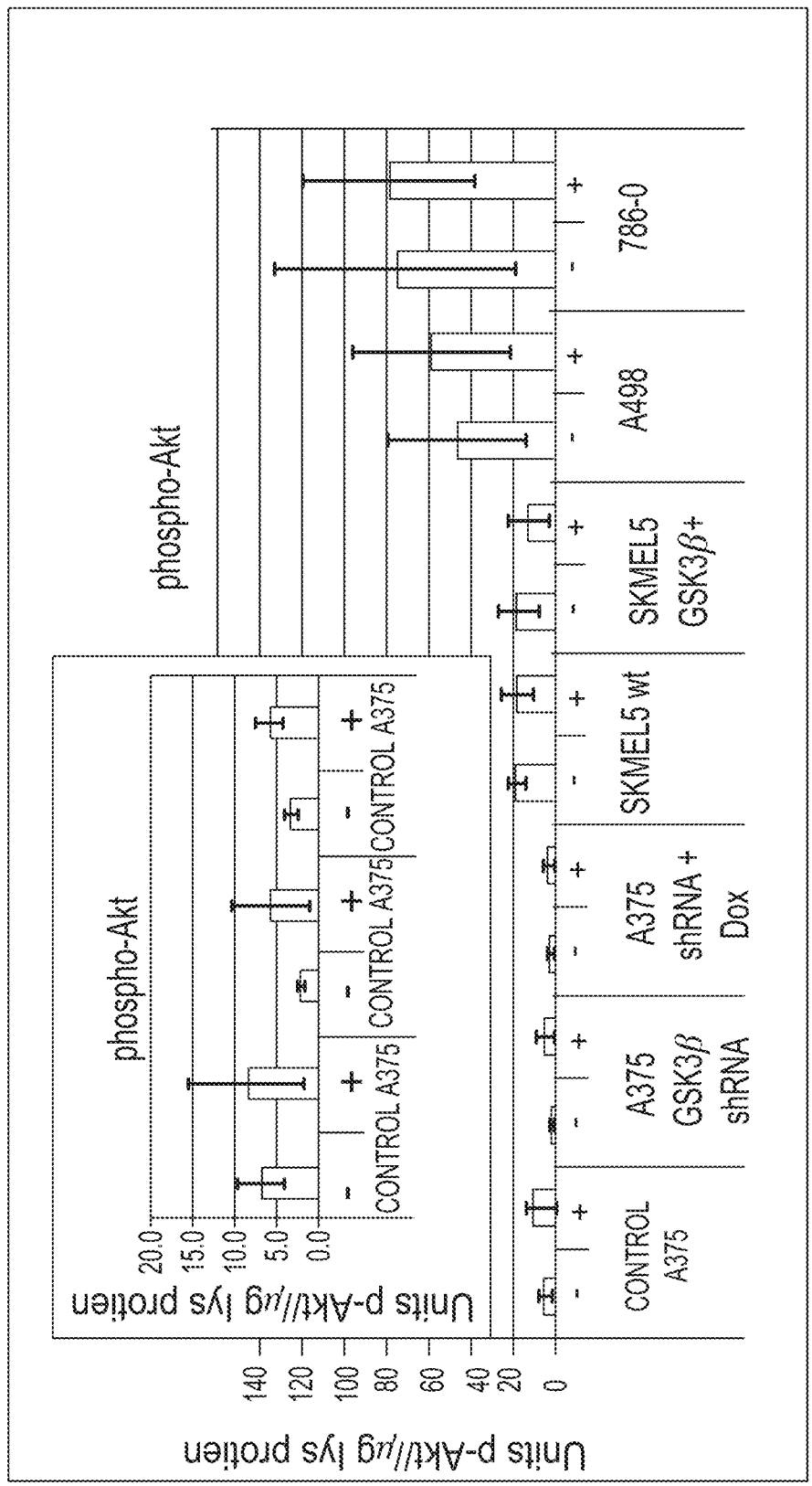
Figure 1I:
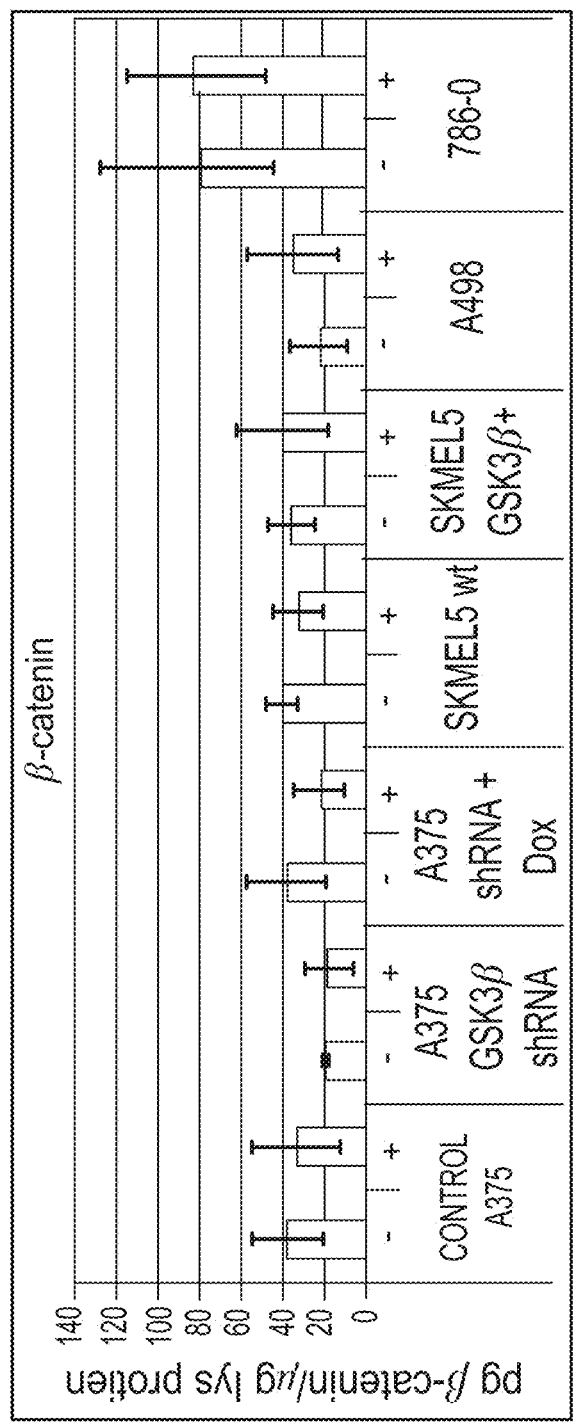
Figure 1J:
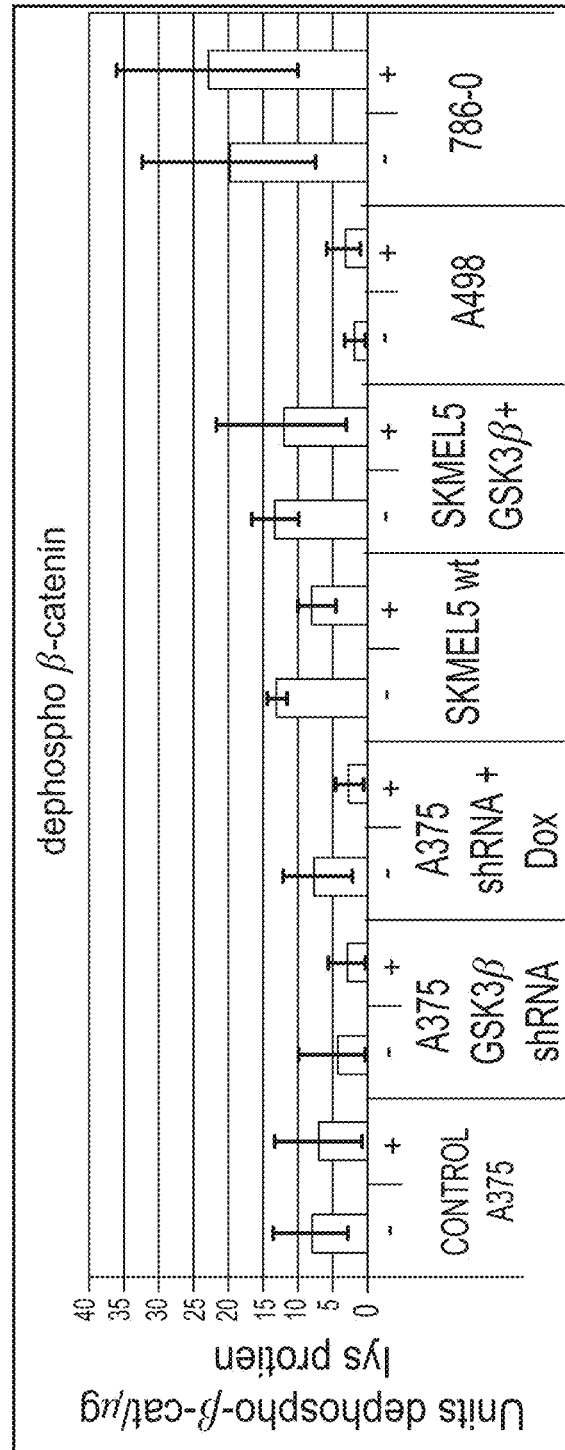
Figure 1K:
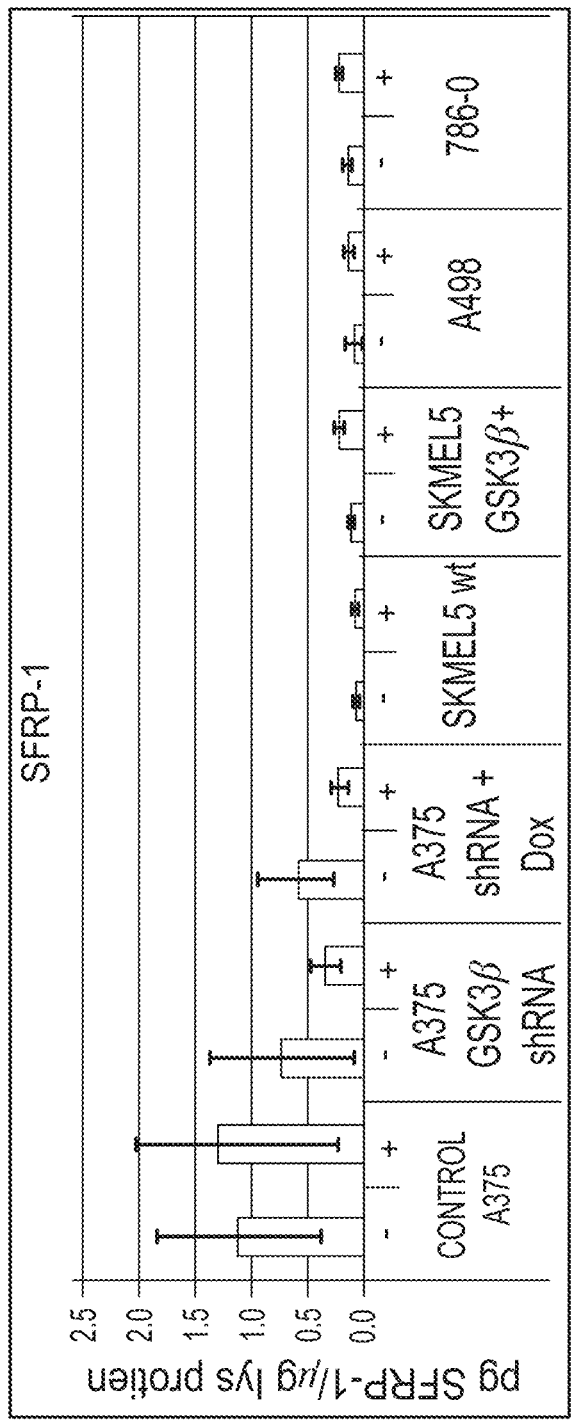
Figure 1L:
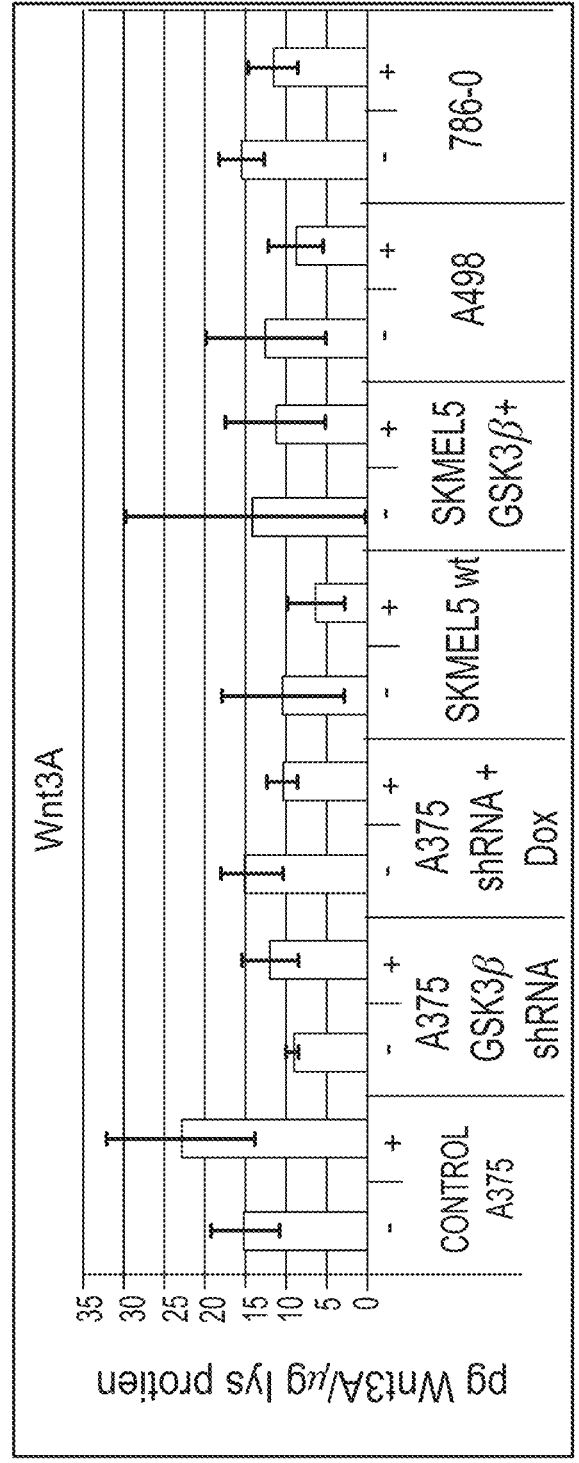
Figure 1M:
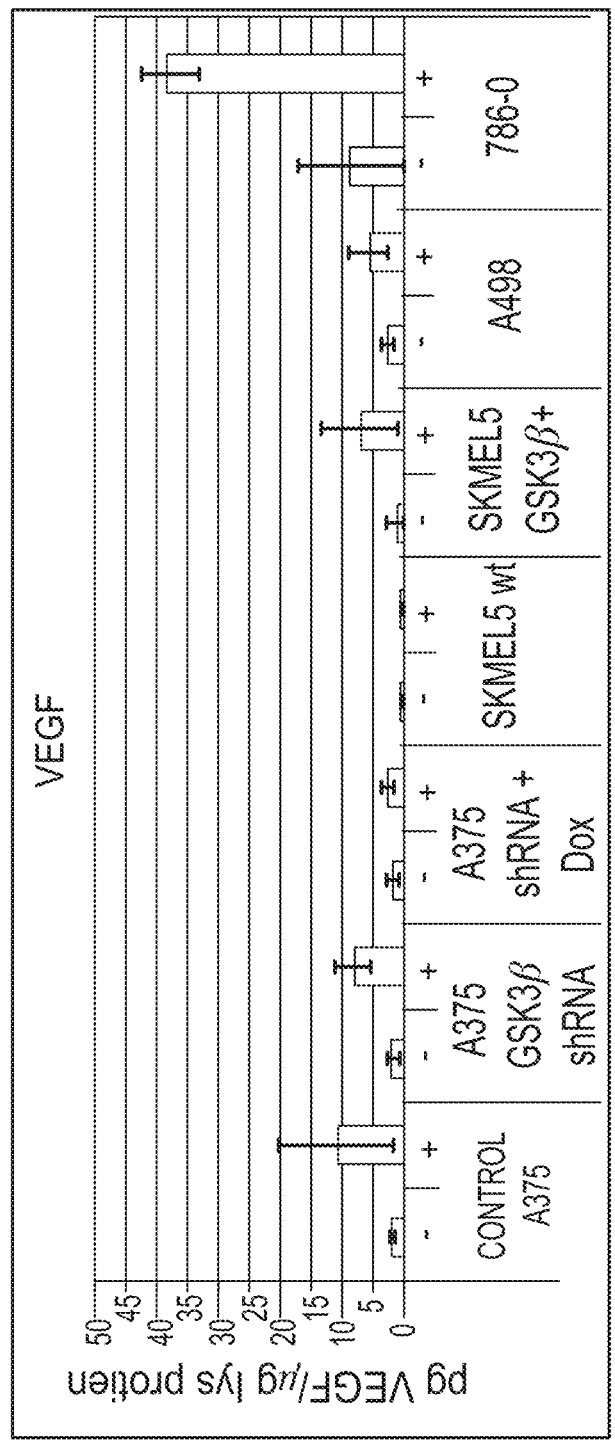
Figure 1N:
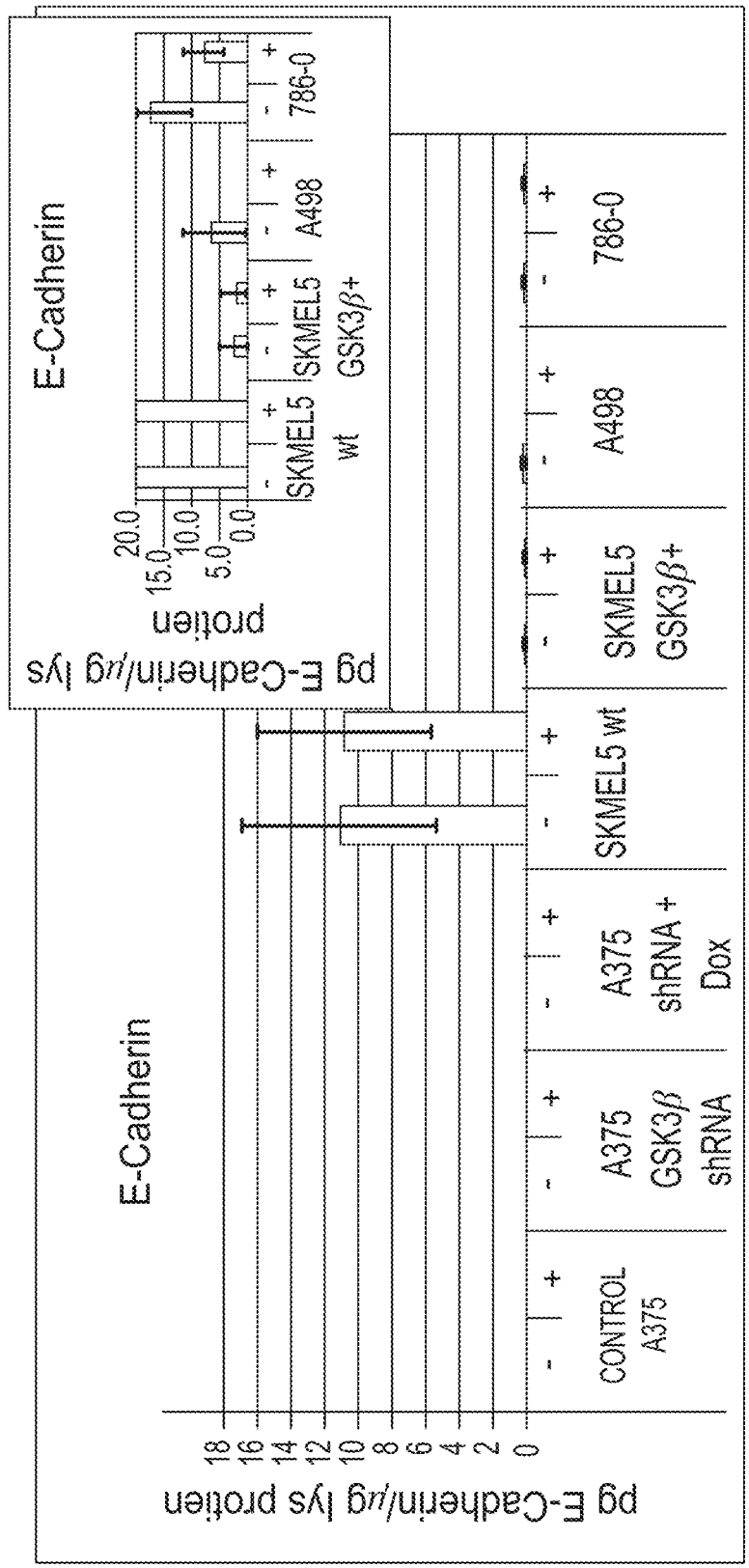

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

As used herein, the term "sample" is intended to mean any biological fluid, cell, tissue, organ or combinations or portions thereof, which includes or potentially includes a biomarker of a disease of interest. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. In one embodiment, the samples that are analyzed in the assays of the present invention are blood, peripheral blood mononuclear cells (PBMC), isolated blood cells, serum and plasma. Other suitable samples include biopsy tissue, intestinal mucosa, saliva, cerebral spinal fluid, and urine. In a preferred embodiment, samples used in the assays of the invention are serum samples.

A "biomarker" is a substance that is associated with a particular disease. A change in the levels of a biomarker may correlate with the risk or progression of a disease or with the susceptibility of the disease to a given treatment. A biomarker may be useful in the diagnosis of disease risk or the presence of disease in an individual, or to tailor treatments for the disease in an individual (choices of drug treatment or administration regimes and/or to predict responsiveness or non-responsiveness to a particular therapeutic regimen). In evaluating potential drug therapies, a biomarker may be used as a surrogate for a natural endpoint such as survival or irreversible morbidity. If a treatment alters a biomarker that has a direct connection to improved health, the biomarker serves as a "surrogate endpoint" for evaluating clinical benefit. A sample that is assayed in the diagnostic methods of the present invention may be obtained from any suitable patient, including but not limited to a patient suspected of having cancer or a patient having a predisposition to cancer. The patient may or may not exhibit symptoms associated with one or more of these conditions.

"Level" refers to the amount, concentration, or activity of a biomarker. The term "level" may also refer to the rate of change of the amount, concentration or activity of a biomarker. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a biomarker accumulated in a cell, including, for example, the amount of particular post-synthetic modifications of a biomarker such as a polypeptide, nucleic acid or small molecule. The term can be used to refer to an absolute amount of a biomarker in a sample or to a relative amount of the biomarker, including amount or concentration determined under steady-state or non-steady-state conditions. Level may also refer to an assay signal that correlates with the amount, concentration, activity or rate of change of a biomarker. The level of a biomarker can be determined relative to a control marker.

As used herein, the term "cancer" is intended to mean a class of diseases characterized by the uncontrolled growth of aberrant cells, including all known cancers, and neoplastic conditions, whether characterized as malignant, benign, soft tissue or solid tumor. In one embodiment, the cancerous condition is metastatic renal cell carcinoma (RCC). An estimated 54,390 new cases and an estimated more than 13,000 deaths in the United States of RCC were reported in 2008. Of all kidney tumors, 85% are RCC, and of those patients diagnosed with RCC, 25% present with advanced disease. RCC is frequently an incidental finding via ultrasonography and CT scan. Approximately 15% to 48% of new cases are discovered incidentally and 25% to 30% of patients have metastases at initial presentation. In an alternative embodiment, the cancerous condition is melanoma. Melanoma accounts for less than 5% of skin cancer cases but causes a large majority of skin cancer deaths. The American Cancer Society estimates that in 2013, about 76,690 new melanomas will be diagnosed (about 45,060 in men and 31,630 in women) and about 9,480 people are expected to die of melanoma (about 6,280 men and 3,200 women). The rates of melanoma have been rising for at least 30 years. Melanoma is more than 20 times more common in whites than in African Americans. Overall, the lifetime risk of getting melanoma is about 2% (1 in 50) for whites, 0.1% (1 in 1,000) for blacks, and 0.5% (1 in 200) for Hispanics. Unlike many other common cancers, melanoma occurs in both younger and older people. Rates continue to increase with age and are highest among those in their 80s, but melanoma is not uncommon even among those younger than 30. In fact, it is one of the more common cancers in young adults (especially young women).

The levels of pharmacodynamic markers can be assessed to determine the effects of investigational agents, assaying tumors directly or surrogate tissues such as plasma. The ultimate goal is to incorporate predictive pharmacodynamic markers in early clinical studies of new oncology drugs. This would allow early evaluation of investigational agents based on human pharmacology data in a 'real time' setting. The biomarkers identified herein can be used for cancer diagnostics, e.g., to predict (prior to treatment) and/or determine (after commencement of treatment) whether a cancer is resistant to a specific course of treatment. The following biomarkers were identified as valuable in the diagnosis and prediction of responsiveness to treatment for melanoma and renal cell carcinoma: total and/or phosphorylated Akt, Erk1/2, STAT3, GSK3β, Hif1α, p21, AMPKa1, VEGF, PlGF, VEGFR-1/Flt-1, c-Met, beta-catenin, SFRP-1, Akt, Wnt3A, Rb, E-cadherin, and combinations thereof. In a preferred embodiment, the biomarkers used in the instant invention include c-Met, beta-catenin, SFRP-1, Akt, Wnt3A, Rb, VEGF, E-cadherin, GSK3beta, and combinations thereof. The invention includes the use of these biomarkers (or other proteins associated with the VEGF and/or RAF/MEK/ERK signaling pathways) to indicate if treatment with a therapeutic regimen targeting the VEGF signaling pathways and/or the RAF/MEK/ERK pathway results in responsive or non-responsive outcomes. Analysis of human tumor xenograft samples from mice in assays for total and/or phosphorylated Akt, Erk1/2, STAT3, GSK3β, Hif1α, p21, AMPKa1, VEGF, PlGF, VEGFR-1/Flt-1, c-Met, beta-catenin, SFRP-1, Akt, Wnt3A, Rb, E-cadherin, GSK3beta, and other pharmacodynamic factors shows that these proteins are biomarkers for RCC and/or metastatic melanoma and that the levels of these proteins can be used to determine the responsiveness or non-responsiveness of cancers (including RCC and metastatic melanoma) to such treatment.

Accordingly, the present invention includes a method and kit configured to measure the levels of one or more of total and/or phosphorylated Akt, Erk1/2, STAT3, GSK3β, Hif1α, p21, AMPKa1, VEGF, PlGF, VEGFR-1/Flt-1, c-Met, beta-catenin, SFRP-1, Akt, Wnt3A, Rb, E-cadherin, GSK3beta, to determine if a tumor is responsive and/or non-responsive to treatment with drugs targeting the VEGF or RAF/MEK/ERK pathways (e.g., sorafenib). In addition, the invention also relates to methods and kits to detect abnormal GSK3beta activity in a patient and/or to detect an alteration in GSK3beta activity by measuring one or more of the biomarkers identified above and comparing those levels to a normal control and/or a baseline level to determine if an abnormality or alteration is present in a patient sample.

Therefore, the invention provides a method for evaluating the efficacy of a treatment regimen in a patient diagnosed with RCC and/or metastatic melanoma, said method comprising (a) measuring a level of a biomarker in a test sample obtained from a patient undergoing said treatment regimen for RCC or metastatic melanoma, wherein said biomarker is selected from the group consisting of total and/or phosphorylated Akt, Erk1/2, STAT3, GSK3β, Hif1α, p21, AMPKa1, VEGF, PlGF, VEGFR-1/Flt-1, c-Met, beta-catenin, SFRP-1, Akt, Wnt3A, Rb, E-cadherin, GSK3beta, and combinations thereof; and (b) evaluating from said level whether said patient is responsive to said treatment regimen. In addition, the invention also provides a method for identifying an abnormality/alteration in GSK3beta activity in a patient diagnosed with RCC and/or metastatic melanoma, said method comprising (a) measuring a level of a biomarker in a test sample obtained from a patient undergoing said treatment regimen for RCC or metastatic melanoma, wherein said biomarker is selected from the group consisting of total and/or phosphorylated Akt, Erk1/2, STAT3, GSK3β, Hif1α, p21, AMPKa1, VEGF, PlGF, VEGFR-1/Flt-1, o-Met, beta-catenin, SFRP-1, Akt, Wnt3A, Rb, E-cadherin, GSK3beta, and combinations thereof; and (b) evaluating from said level whether said level is abnormal and/or altered relative to a normal or baseline level.

In one embodiment, the method includes measuring a level of a first biomarker and an additional biomarker, wherein the first biomarker is a total form of a biomarker and the additional biomarker is a phosphorylated form of that biomarker. Diagnosis of the presence or state of a cancer could be based on the absolute levels of one or both of these forms. Alternatively, the diagnosis could be based on the ratio of phosphorylated to total forms (i.e., based on the fraction of a specific biomarker that is present in a phosphorylated form). In one example, the method may include measuring a level of total Akt as the first biomarker and measuring a level of phosphorylated Akt as the additional biomarker. Similarly, the method may comprise measuring one or more of the following pairs of first and additional biomarkers, i.e., total and phosphorylated biomarkers: total Erk1/2 and phosphorylated Erk1/2; total Met and phosphorylated Met; total GSK3β and phosphorylated GSK3β; and total AMPKa1 and phosphorylated AMPKa1.

The level(s) of the various biomarkers identified herein may reflect the responsiveness or non-responsiveness of RCC and/or melanoma to a given treatment regimen. A response to a therapeutic regimen includes a detectable reduction to some extent of one or more of the symptoms of RCC, including, but not limited to: (1) reduction in the number of cancer cells; (2) reduction in tumor size; (3) inhibition (i.e., slowing to some extent, preferably stopping) of cancer cell infiltration into peripheral organs; (4) inhibition (i.e., slowing to some extent, preferably stopping) of tumor metastasis; (5) inhibition, to some extent, of tumor growth; (6) relieving or reducing to some extent one or more of the symptoms associated with the disorder; and/or (7) increasing, to some extent, the overall survival of a patient relative to that observed for the standard of care for RCC or melanoma. A response to a therapeutic regimen may also comprise maintenance of a therapeutic benefit, including, but not limited to (1) inhibiting an increase in the number of cancer cells; (2) inhibiting an increase in tumor size; (3) inhibiting cancer cell infiltration into peripheral organs; (4) inhibiting tumor metastases; (5) relieving or reducing to some extent one or more of the symptoms associated with the disorder; and/or (6) inhibiting a recurrence or onset of one or more of the symptoms associated with the disorder.

The therapeutic regimen used in the method of the present invention may include radiation treatment, chemotherapy, treatment with therapeutic drugs, immune system modulation or other therapeutic regimes used in cancer treatment. In one embodiment, the therapeutic regimen comprises administration of a therapeutic agent that modulates one or more biological activities and/or one or more signaling pathways and the level(s) of said one or more biomarkers indicate modulation of said biological activities and/or said signaling pathways by said therapeutic agent. In particular, the signaling pathways may include the VEGF-signaling pathway and Ras/Raf/MEK/ERK signaling pathway and the therapeutic agent may be an agonist or an antagonist of such signaling pathway(s).

The therapeutic regimen may include administration of a therapeutic agent or a combination of therapeutic agents to a patient one or more times over a given time period. For example, if the therapeutic agent is sorafenib, one suitable therapeutic regimen comprises administering the drug twice daily until the patient is no longer clinically benefiting from treatment or until unacceptable toxicity occurs. This treatment regimen may be accompanied by the administration of one or more additional chemotherapeutic agents or palliative agents. The level(s) of biomarkers may be measured before treatment, one or more times during the administration period, and/or after treatment is suspended. If sunitinib is the selected therapeutic agent, one example of a suitable therapeutic regimen comprises administration of the drug once daily for four weeks, followed by a two week period in which sunitinib is not administered to the patient. This cycle may be repeated one or more times. This treatment regimen may also be accompanied by the administration of one or more additional chemotherapeutic agents or palliative agents. The level(s) of biomarkers may be measured at one or more time points in the treatment regimen, e.g., before treatment, one or more times during the four week administration period, and/or after the four week administration period. Therefore, the method may include measuring an interim level of a biomarker during the therapeutic regimen and the evaluating step further comprises comparing that level, the interim level and the baseline level.

In addition, the level of a biomarker may be determined at any time point before and/or after initiation of treatment. In one embodiment, the biomarker is used to gauge the efficacy of a therapeutic regimen. Therefore, the method of the present invention may include measuring a baseline level(s) of a biomarker before a therapeutic regimen is initiated, and the evaluating step further comprises comparing the level and the baseline level. Moreover, the method may further comprise measuring an interim level of the biomarker during the therapeutic regimen and the evaluating step further comprises comparing the level, the interim level and the baseline level.

Alternatively, the measuring step may comprise measuring a level(s) of a biomarker before a therapeutic regimen is initiated to predict whether RCC or melanoma will be responsive or non-responsive to a given therapeutic regimen. The method may further comprise modifying the therapeutic regimen based on the level(s) of a biomarker observed during the measuring step, e.g., increasing or decreasing the dosage, frequency, or route of administration of a therapeutic agent, adding an additional therapeutic agent and/or palliative agent to a treatment regimen, or if the therapeutic regimen includes the administration of two or more therapeutic and/or palliative agents, the treatment regimen may be modified to eliminate one or more of the therapeutic and/or palliative agents used in the combination therapy.

Still further, the evaluating step may include comparing the level of a biomarker to a detection cut-off level, wherein a level above the detection cut-off level is indicative of RCC or melanoma. Alternatively, the evaluating step comprises comparing a level of a biomarker to a detection cut-off level, wherein a level below the detection cut-off level is indicative of RCC or melanoma.

In one embodiment of the present invention, the level of a biomarker is compared to a detection cut-off level or range, wherein the biomarker level above or below the detection cut-off level (or within the detection cut-off range) is indicative of RCC or melanoma. Furthermore, the levels of two or more biomarkers may both be used to make a determination. For example, i) having a level of at least one of the markers above or below a detection cut-off level (or within a detection cut-off range) for that marker is indicative of RCC or melanoma; ii) having the level of two or more (or all) of the markers above or below a detection cut-off level (or within a detection cut-off range) for each of the markers is indicative of RCC or melanoma; or iii) an algorithm based on the levels of the multiple markers is used to determine if RCC or melanoma is present.

As described herein, the measured levels of one or more biomarkers may be used to detect or monitor cancer (e.g., RCC or melanoma) and/or to determine the responsiveness of a cancer to a specific treatment regimen. The specific methods/algorithms for using biomarker levels to make these determinations, as described herein, may optionally be implemented by software running on a computer that accepts the biomarker levels as input and returns a report with the determinations to the user. This software may run on a standalone computer or it may be integrated into the software/computing system of the analytical device used to measure the biomarker levels or, alternatively, into a laboratory information management system (LIMS) into which crude or processed analytical data is entered. In one embodiment, biomarkers are measured in a point-of-care clinical device which carries out the appropriate methods/algorithms for detecting, monitoring or determining the responsiveness of a cancer and which reports such determination(s) back to the user.

In addition, the methods of the present invention may be used in combination with other methods of diagnosing RCC or melanoma in a patient. In one embodiment, the patient may also be subjected to one or more diagnostic tools designed to detect RCC or melanoma. For example, imaging methods may be used to provide images of the kidney to look for tumors. In addition, a kidney or skin biopsy may be performed. Imaging methods that may be performed include ultrasound, computed tomography (CT) scan and magnetic resonance imaging (MRI).

The assays of the present invention may be conducted by any suitable method. In one embodiment, the measuring step is conducted on a single sample, and it may be conducted in a single assay chamber or assay device, including but not limited to a single well of an assay plate, a single assay cartridge, a single lateral flow device, a single assay tube, etc.

According to one aspect of the invention, the level(s) of biomarker(s) are measured in samples collected from individuals clinically diagnosed with, suspected of having or at risk of developing RCC or melanoma. Initial diagnosis may have been carried out using conventional methods, e.g., biopsy or other conventional diagnostic methods. The level(s) of biomarker(s) are also measured in healthy individuals. Specific biomarkers valuable in distinguishing between normal and diseased patients are identified by visual inspection of the data, for example, by visual classification of data plotted on a one-dimensional or multidimensional graph, or by using statistical methods such as characterizing the statistically weighted difference between control individuals and diseased patients and/or by using Receiver Operating Characteristic (ROC) curve analysis. A variety of suitable methods for identifying useful biomarkers and setting detection thresholds/algorithms are known in the art and will be apparent to the skilled artisan.

For example and without limitation, diagnostically valuable biomarkers may be first identified using a statistically weighted difference between control individuals and diseased patients, calculated as $$\frac{D-N}{\sqrt{\sigma_D * \sigma_N}}$$

wherein D is the median level of a biomarker in patients diagnosed as having, for example, kidney cancer, N is the median (or average) of the control individuals, $\sigma_D$ is the standard deviation of D and $\sigma_N$ is the standard deviation of N. The larger the magnitude, the greater the statistical difference between the diseased and normal populations.

According to one embodiment of the invention, biomarkers resulting in a statistically weighted difference between control individuals and diseased patients of greater than, e.g., 1, 1.5, 2, 2.5 or 3 could be identified as diagnostically valuable markers.

Another method of statistical analysis for identifying biomarkers is the use of z-scores, e.g., as described in Skates et al. (2007) Cancer Epidemiol. Biomarkers Prev. 16(2):334-341.

Another method of statistical analysis that can be useful in the inventive methods of the invention for determining the efficacy of particular candidate analytes, such as particular biomarkers, for acting as diagnostic marker(s) is ROC curve analysis. An ROC curve is a graphical approach to looking at the effect of a cut-off criterion, e.g., a cut-off value for a diagnostic indicator such as an assay signal or the level of an analyte in a sample, on the ability of a diagnostic to correctly identify positive or negative samples or subjects. One axis of the ROC curve is the true positive rate (TPR, i.e., the probability that a true positive sample/subject will be correctly identified as positive, or alternatively, the false negative rate (FNR=1−TPR, the probability that a true positive sample/subject will be incorrectly identified as a negative). The other axis is the true negative rate, i.e., TNR, the probability that a true negative sample will be correctly identified as a negative, or alternatively, the false positive rate (FPR=1−TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR or FNR and TNR or FPR for each cut-off value. The area under the ROC curve (referred to herein as the AUC) is one indication of the ability of the diagnostic to separate positive and negative samples/subjects. In one embodiment, a biomarker provides an AUC ≥0.7. In another embodiment, a biomarker provides an AUC ≥0.8. In another embodiment, a biomarker provides an AUC ≥0.9.

Diagnostic indicators analyzed by ROC curve analysis may be a level of an analyte, e.g., a biomarker, or an assay signal. Alternatively, the diagnostic indicator may be a function of multiple measured values, for example, a function of the level/assay signal of a plurality of analytes, e.g., a plurality of biomarkers, or a function that combines the level or assay signal of one or more analytes with a patient's scoring value that is determined based on visual, radiological and/or histological evaluation of a patient. The multi-parameter analysis may provide more accurate diagnosis relative to analysis of a single marker.

Candidates for a multi-analyte panel could be selected by using criteria such as individual analyte ROC areas, median difference between groups normalized by geometric interquartile range (IQR) etc. The objective is to partition the analyte space to improve separation between groups (for example, normal and disease populations) or to minimize the misclassification rate.

One approach is to define a panel response as a weighted combination of individual analytes and then compute an objective function like ROC area, product of sensitivity and specificity, etc. See e.g., WO 2004/058055, as well as US2006/0205012, the disclosures of which are incorporated herein by reference in their entireties.

Biomarker levels may be measured using any of a number of techniques available to the person of ordinary skill in the art, e.g., direct physical measurements (e.g., mass spectrometry) or binding assays (e.g., immunoassays, agglutination assays and immunochromatographic assays). The method may also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring biomarker levels may use solid phase or homogenous formats. Suitable assay methods include sandwich or competitive binding assays. Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601, 4,442,204 and 5,208,535, each of which are incorporated herein by reference in their entireties.

Multiple biomarkers may be measured using a multiplexed assay format, e.g., multiplexing through the use of binding reagent arrays, multiplexing using spectral discrimination of labels, multiplexing of flow cytometric analysis of binding assays carried out on particles, e.g., using the Luminex® system. Suitable multiplexing methods include array based binding assays using patterned arrays of immobilized antibodies directed against the biomarkers of interest. Various approaches for conducting multiplexed assays have been described (See e.g., US 20040022677; US 20050052646; US 20030207290; US 20030113713; US 20050142033; and US 20040189311, each of which is incorporated herein by reference in their entireties. One approach to multiplexing binding assays involves the use of patterned arrays of binding reagents, e.g., U.S. Pat. Nos. 5,807,522 and 6,110,426; Delehanty J-B., Printing functional protein microarrays using piezoelectric capillaries, Methods Mol. Bio. (2004) 278: 135-44; Lue R Y et al., Site-specific immobilization of biotinylated proteins for protein microarray analysis, Methods Mol. Biol. (2004) 278: 85-100; Lovett, Toxicogenomics: Toxicologists Brace for Genomics Revolution, Science (2000) 289: 536-537; Berns A, Cancer: Gene expression in diagnosis, nature (2000), 403, 491-92; Walt, Molecular Biology: Bead-based Fiber-Optic Arrays, Science (2000) 287: 451-52 for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A A, "Multiplexed Particle-Based Flow Cytometric Assays" J. ImmunoL Meth. (2000) 243: 243-55). A similar approach involving a set of 15 different beads of differing size and fluorescence has been disclosed as useful for simultaneous typing of multiple pneumococcal serotypes (Park, M. K et al., "A Latex Bead-Based Flow Cytometric Immunoassay Capable of Simultaneous Typing of Multiple Pneumococcal Serotypes (Multibead Assay)" Clin. Diag. Lab ImmunoL (2000) 7: 4869). Bishop, J E et al. have described a multiplex sandwich assay for simultaneous quantification of six human cytokines (Bishop, L E. et al., "Simultaneous Quantification of Six Human Cytokines in a Single Sample Using Microparticle-based Flow Cytometric Technology," Clin. Chem (1999) 45:1693-1694).

A diagnostic test may be conducted in a single assay chamber, such as a single well of an assay plate or an assay chamber that is an assay chamber of a cartridge. The assay modules, e.g., assay plates or cartridges or multi-well assay plates), methods and apparatuses for conducting assay measurements suitable for the present invention are described for example, in US 20040022677; US 20050052646; US 20050142033; US 20040189311, each of which is incorporated herein by reference in their entireties. Assay plates and plate readers are now commercially available (MULTI-SPOT® and MULTI-ARRAY® plates and SECTOR® instruments, Meso Scale Discovery, a division of Meso Scale Diagnostics, LLC, Rockville, Md.).

The present invention relates to a kit for the analysis of a panel of target analytes. The kit is preferably configured to conduct a multiplexed assay of two or more of the following analytes: total, phosphorylated, and dephosphorylated isoforms of c-Met, beta-catenin, SFRP-1, Akt, Wnt3A, Rb, VEGF, E-cadherin, GSK3beta, and combinations thereof. The kit can include (a) a single panel arrayed on a multi-well plate which is configured to be used in an electrochemiluminescence assay, as well as (b) associated consumables, e.g., detection antibodies, calibrators, and optional diluents and/or buffers. Alternatively, the multi-well plates and associated consumables can be provided separately.

The panel is preferably configured in a multi-well assay plate including a plurality of wells, each well having an array with "spots" or discrete binding domains. Preferably, the array includes one, four, seven, ten, sixteen, or twenty-five binding domains, and most preferably, the array includes one, four, seven, or ten binding domains. A capture antibody to each analyte is immobilized on a binding domain in the well and that capture antibody is used to detect the presence of the target analyte in an immunoassay. Briefly, a sample suspected of containing that analyte is added to the well and if present, the analyte binds to the capture antibody at the designated binding domain. The presence of bound analyte on the binding domain is detected by adding labeled detection antibody. The detection antibody also binds to the analyte forming a "sandwich" complex (capture antibody-analyte-detection antibody) on the binding domain.

The multiplexed immunoassay kits described herein allow a user to simultaneously quantify multiple biomarkers. The panels are selected and optimized such that the individual assays function well together. The sample may require dilution prior to being assayed. Sample dilutions for specific sample matrices of interest are optimized for a given panel to minimize sample matrix effects and to maximize the likelihood that all the analytes in the panel will be within the dynamic range of the assay. In a preferred embodiment, all of the analytes in the panel are analyzed with the same sample dilution in at least one sample type. In another preferred embodiment, all of the analytes in a panel are measured using the same dilution for most sample types.

For a given panel, the detection antibody concentration and the number of labels per protein (L/P ratio) for the detection antibody are adjusted to bring the expected levels of all analytes into a quantifiable range at the same sample dilution. If one wants to increase the high end of the quantifiable range for a given analyte, then the UP can be decreased and/or the detection antibody concentration is decreased. On the other hand, if one wants to increase the lower end of the quantifiable range, the UP can be increased, the detection antibody concentration can be increased if it is not at the saturation level, and/or the background signal can be lowered.

Calibration standards for use with the assay panels are selected to provide the appropriate quantifiable range with the recommended sample dilution for the panel. The calibration standards have known concentrations of one of more of the analytes in the panel. Concentrations of the analytes in unknown samples are determined by comparison to these standards. In one embodiment, calibration standards comprise mixtures of the different analytes measured by an assay panel. Preferably, the analyte levels in a combined calibrator are selected such that the assay signals for each analyte are comparable, e.g., within a factor of two, a factor of five or a factor of 10. In another embodiment, calibration standards include mixtures of analytes from multiple different assay panels.

A calibration curve may be fit to the assay signals measured with calibration standards using, e.g., curve fits known in the art such as linear fits, 4-parameter logistic (4-PL) and 5-parameter (5-PL) fits. Using such fits, the concentration of analytes in an unknown sample may be determined by backfitting the measured assay signals to the calculated fits. Measurements with calibration standards may also be used to determine assay characteristics such as the limit of detection (LOD), limit of quantification (LOQ), dynamic range, and limit of linearity (LOL).

A kit can include the following assay components: a multi-well assay plate configured to conduct an immunoassay for one of the panels described herein, a set of detection antibodies for the analytes in the panel (wherein the set comprises individual detection antibodies and/or a composition comprising a blend of one or more individual detection antibodies), and a set of calibrators for the analytes in the panel (wherein the set comprises individual calibrator protein compositions and/or a composition comprising a blend of one or more individual calibrator proteins). The kit can also include one of more of the following additional components: a blocking buffer (used to block assay plates prior to addition of sample), an antibody diluent (used to dilute stock detection antibody concentrations to the working concentration), an assay diluent (used to dilute samples), a calibrator diluent (used to dilute or reconstitute calibration standards) and a read buffer (used to provide the appropriate environment for detection of assay labels, e.g., by an ECL measurement). The antibody and assay diluents are selected to reduce background, optimize specific signal, and reduce assay interference and matrix effect. The calibrator diluent is optimized to yield the longest shelf life and retention of calibrator activity. The blocking buffer should be optimized to reduce background. The read buffer is selected to yield the appropriate sensitivity, quantifiable range, and slowest off-rate.

The reagent components of the kit can be provided as liquid reagents, lyophilized, or combinations thereof, diluted or undiluted, and the kit includes instructions for appropriate preparation of reagents prior to use. In a preferred embodiment, a set of detection antibodies are included in the kit comprising a plurality of individual detection antibody compositions in liquid form. Moreover, the set of calibrators provided in the kit preferably comprise a lyophilized blend of calibrator proteins. Still further, the kit includes a multi-well assay plate that has been pre-coated with capture antibodies and exposed to a stabilizing treatment to ensure the integrity and stability of the immobilized antibodies.

As part of a multiplexed panel development, assays are optimized to reduce calibrator and detection antibody non-specific binding. In sandwich immunoassays, specificity mainly comes from capture antibody binding. Some considerations for evaluating multiplexed panels include: (a) detection antibody non-specific binding to capture antibodies is reduced to lower background of assays in the panel, and this can be achieved by adjusting the concentrations and L/P of the detection antibodies; (b) non-specific binding of detection antibodies to other calibrators in the panel is also undesirable and should be minimized; (c) non-specific binding of other calibrators in the panel and other related analytes should be minimized; if there is calibrator non-specific binding, it can reduce the overall specificity of the assays in the panel and it can also yield unreliable results as there will be calibrator competition to bind the capture antibody.

Different assays in the panel may require different incubation times and sample handling requirements for optimal performance. Therefore, the goal is to select a protocol that's optimized for most assays in the panel. Optimization of the assay protocol includes, but is not limited to, adjusting one or more of the following protocol parameters: timing (incubation time of each step), preparation procedure (calibrators, samples, controls, etc.), and number of wash steps.

The reagents used in the kits, e.g., the detection and capture antibodies and calibrator proteins, are preferably subjected to analytical testing and meet or exceed the specifications for those tests. The analytical tests that can be used to characterize kit materials include but are not limited to, CIEF, DLS, reducing and/or non-reducing EXPERION, denaturing SDS-PAGE, non-denaturing SDS-PAGE, SEC-MALS, and combinations thereof. In a preferred embodiment, the materials are characterized by CIEF, DLS, and reducing and non-reducing EXPERION. One or more additional tests, including but not limited to denaturing SDS-PAGE, non-denaturing SDS-PAGE, SEC-MALS, and combinations thereof, can also be used to characterize the materials. In a preferred embodiment, the materials are also subjected to functional testing, i.e., a binding assay for the target analyte, as well as one or more characterization tests, such as those listed above. If the materials do not meet or exceed the specifications for the functional and/or characterization tests, they can be subjected to additional purification steps and re-tested. Each of these tests and the metrics applied to the analysis of raw materials subjected to these tests are described below:

Capillary Isoelectric Focusing (CIEF) is a technique commonly used to separate peptides and proteins, and it is useful in the detection of aggregates. During a CIEF separation, a capillary is filled with the sample in solution and when voltage is applied, the ions migrate to a region where they become neutral (pH=pl). The anodic end of the capillary sits in acidic solution (low pH), while the cathodic end sits in basic solution (high pH). Compounds of equal isoelectric points (pl) are "focused" into sharp segments and remain in their specific zone, which allows for their distinct detection based on molecular charge and isoelectric point Each specific antibody solution will have a fingerprint CIEF that can change over time. When a protein solution deteriorates, the nature of the protein and the charge distribution can change. Therefore, CIEF is a particularly useful tool to assess the relative purity of a protein solution and it is a preferred method of characterizing the antibodies and calibrators in the plates and kits described herein. The metrics used in CIEF include pl of the main peak, the pl range of the solution, and the profile shape, and each of these measurements are compared to that of a reference standard.

Dynamic Light Scattering (DLS) is used to probe the diffusion of particulate materials either in solution or in suspension. By determining the rate of diffusion (the diffusion coefficient), information regarding the size of particles, the conformation of macromolecular chains, various interactions among the constituents in the solution or suspension, and even the kinetics of the scatterers can be obtained without the need for calibration. In a DLS experiment, the fluctuations (temporal variation, typically in a μs to ms time scale) of the scattered light from scatterers in a medium are recorded and analyzed in correlation delay time domain. Like CIEF, each protein solution will generate a fingerprint DLS for the particle size and it's ideally suited to detect aggregation. All IgGs, regardless of binding specificity, will exhibit the same DLS particle size. The metrics used to analyze a protein solution using DLS include percentage polydispersity, percentage intensity, percentage mass, and the radius of the protein peak. In a preferred embodiment, an antibody solution meets or exceeds one or more of the following DLS specifications: (a) radius of the antibody peak: 4-8 nm (antibody molecule size); (b) polydispersity of the antibody peak: <40% (measure of size heterogeneity of antibody molecules); (c) intensity of the antibody peak: >50% (if other peaks are present, then the antibody peak is the predominant peak); and (d) mass in the antibody peak: >50%.

Reducing and non-reducing gel electrophoresis are techniques well known in the art. The EXPERION™ (Bio-Rad Laboratories, Inc., www.bio-rad.com) automated electrophoresis station performs all of the steps of gel-based electrophoresis in one unit by automating and combining electrophoresis, staining, destaining, band detection, and imaging into a single step. It can be used to measure purity. Preferably, an antibody preparation is greater 50% pure by Experion, more preferably, greater than 75% pure, and most preferably greater than 80% pure. Metrics that are applied to protein analysis using non-reducing Experion include percentage total mass of protein, and for reducing Experion they include percentage total mass of the heavy and light chains in an antibody solution, and the heavy to light chain ratio.

Multi-Angle Light Scattering (MALS) detection can be used in the stand-alone (batch) mode to measure specific or non-specific protein interactions, as well as in conjunction with a separation system such as flow field flow fractionation (FFF) or size exclusion chromatography (SEC). The combined SEC-MALS method has many applications, such as the confirmation of the oligomeric state of a protein, quantification of protein aggregation, and determination of protein conjugate stoichiometry. Preferably, this method is used to detect molecular weight of the components of a sample.

As used herein, a lot of kits comprise a group of kits comprising kit components that meet a set of kit release specifications. A lot can include at least 10, at least 100, at least 500, at least 1,000, at least 5,000, or at least 10,000 kits and a subset of kits from that lot are subjected to analytical testing to ensure that the lot meets or exceeds the release specifications. In one embodiment, the release specifications include but are not limited to kit processing, reagent stability, and kit component storage condition specifications. Kit processing specifications include the maximum total sample incubation time and the maximum total time to complete an assay using the kit. Reagent stability specifications include the minimum stability of each reagent component of the kit at a specified storage temperature. Kit storage condition specifications include the range of storage temperatures for all components of the kit, the maximum storage temperature for frozen components of the kit, and the maximum storage temperature for non-frozen components of the kit. A subset of kits in a lot is reviewed in relation to these specifications and the size of the subset depends on the lot size. In a preferred embodiment, for a lot of up to 300 kits, a sampling of 4-7 kits are tested; for a lot of 300-950 kits, a sampling of 8-10 kits are tested; and for a lot of greater than 950 kits, a sampling of 10-12 kits are tested. Alternatively or additionally, a sampling of up to 1-5% preferably up to 1-3%, and most preferably up to 2% is tested.

In addition, each lot of multi-well assay plates is preferably subjected to uniformity and functional testing. A subset of plates in a lot is subjected to these testing methods and the size of the subset depends on the lot size. In a preferred embodiment, for a lot of up to 300 plates, a sampling of 4-7 plates are tested; for a lot of 300-950 plates, a sampling of 8-10 plates are tested; and for a lot of greater than 950 plates, a sampling of 10-12 plates are tested. Alternatively or additionally, a sampling of up to 1-5% preferably up to 1-3%, and most preferably up to 2% is tested. The uniformity and functional testing specifications are expressed in terms of % CV, Coefficient of Variability, which is a dimensionless number defined as the standard deviation of a set of measurements, in this case, the relative signal detected from binding domains across a plate, divided by the mean of the set.

One type of uniformity testing is protein NG testing. Protein A/G binding is used to confirm that all binding domains within a plate are coupled to capture antibody. Protein A/G is a recombinant fusion protein that combines IgG binding domains of Protein A and protein G and it binds to all subclasses of human IgG, as well as IgA, IgE, IgM and, to a lesser extent, IgD. Protein A/G also binds to all subclasses of mouse IgG but not mouse IgA, IgM, or serum albumin, making it particularly well suited to detect mouse monoclonal IgG antibodies without interference from IgA, IgM, and serum albumin that might be present in the sample matrix. Protein A/G can be labeled with a detectable moiety, e.g., a fluorescent, chemiluminescent, or electrochemiluminescent label, preferably an ECL label, to facilitate detection. Therefore, if capture antibody is adhered to a binding domain of a well, it will bind to labeled protein A/G, and the relative amount of capture antibody bound to the surface across a plate can be measured.

In addition to the uniformity testing described above, a uniformity metric for a subset of plates within a lot can be calculated to assess within-plate trending. A uniformity metric is calculated using a matrix of normalized signals from protein A/G and/or other uniformity or functional tests. The raw signal data is smoothed by techniques known in the art, thereby subtracting noise from the raw data, and the uniformity metric is calculated by subtracting the minimum signal in the adjusted data set from the maximum signal.

In a preferred embodiment, a subset of plates in a lot is subjected to protein A/G and functional testing and that subset meet or exceed the following specifications:

TABLE 3(a)

Plate Metrics

| Metric | Preferred Specification for a subset of 96 well multi-well plates |
|---|---|
| Average intraplate CV | ≤10% |
| Maximum intraplate CV | ≤13% |
| Average Uniformity | ≤25% |
| Maximum Uniformity | ≤37% |
| CV of intraplate averages | ≤18% |
| Signal, lower boundary | >1500 |
| Signal, upper boundary | <$10^{(6)}$ |

As disclosed in U.S. Pat. No. 7,842,246 to Wohlstadter et al., the disclosure of which is incorporated herein by reference in its entirety, each plate consists of several elements, e.g., a plate top, a plate bottom, wells, working electrodes, counter electrodes, reference electrodes, dielectric materials, electrical connects, and assay reagents. The wells of the plate are defined by holes/openings in the plate top. The plate bottom can be affixed, manually or by automated means, to the plate top, and the plate bottom can serve as the bottom of the well. Plates may have any number of wells of any size or shape, arranged in any pattern or configuration, and they can be composed of a variety of different materials. Preferred embodiments of the invention use industry standard formats for the number, size, shape, and configuration of the plate and wells. Examples of standard formats include 96, 384, 1536, and 9600 well plates, with the wells configured in two-dimensional arrays. Other formats may include single well plates (preferably having a plurality of assay domains that form spot patterns within each well), 2 well plates, 6 well plates, 24 well plates, and 6144 well plates. Each well of the plate includes a spot pattern of varying density, ranging from one spot within a well to 2, 4, 7, 9, 10, 16, 25, etc., as described hereinabove.

Each plate is assembled according to a set of preferred specifications. In a preferred embodiment, a plate bottom meets or exceeds the following specifications:

TABLE 3(b)

Plate bottom specifications

| Parameter | 96-well (round well) specifications in inches |
|---|---|
| Length range (C to C)* | 3.8904-3.9004 (A1-A12 and H1-H12)** |
| Width range (C to C) | 2.4736-2.4836 (A1-A12 and H1-H12) |
| Well to well spacing | 0.3513-0.3573 |

*C to C well distance is the center of spot to center of spot distance between the outermost wells of a plate.

In a further preferred embodiment, the plate also meets or exceeds defined specifications for alignment of a spot pattern within a well of the plate. These specifications include three parameters: (a) $\Delta x$, the difference between the center of the spot pattern and the center of the well along the x axis of the plate (column-wise, long axis); (b) $\Delta y$, the difference between the center of the spot pattern and the center of the well along the y axis of the plate (row-wise, short axis); and (c) $\alpha$, the counter-clockwise angle between the long axis of the plate bottom and the long axis of the plate top of a 96-well plate. In a preferred embodiment, the plate meets or exceeds the following specifications: $\Delta x \leq 0.2$ mm, $\Delta y \leq 0.2$ mm, and $\alpha \leq 0.1°$.

The following non-limiting examples serve to illustrate rather than limit the present invention.

Examples

Measurement of Biomarkers Indicative of Sorafenib Resistance in the Treatment of RCC and Melanoma A panel of biomarkers was measured in Melanoma and RCC xenograft tissue extracts from mice, described in Table 4. Xenografts were generated using the listed melanoma and RCC cell lines, and tumors harvested and extracted following the indicated treatments. SKMEL5 cells were used with or without transfection to express constitutively active GSK3β. A375 cells were used with or without transfection to express GSK3β specific shRNA under a doxycycline-controlled promoter.

TABLE 4

Numbers of individual mouse xenograft extract samples received.

| | xenograft cell line | saline | suntinib | sorafenib | doxycyline | sorafenib + doxycyline |
|---|---|---|---|---|---|---|
| Set 1 Melanoma | SKMEL5 | 4 | — | 4 | — | — |
| | SKMEL5 (active GSK3beta) | 4 | — | 4 | — | — |

TABLE 4-continued

Numbers of individual mouse xenograft extract samples received.

|  | xenograft cell line | saline | suntinib | sorafenib | doxycyline | sorafenib + doxycyline |
|---|---|---|---|---|---|---|
| Set 2 | A375 | 6 | — | 6 | — | — |
| Melanoma | A375 (GSKshRNA) | 4 | — | 4 | 5 | 5 |
| Set 3 | A498 | 5 | 5 | — | — | — |
| RCC | 786-0 | 6 | 6 | — | — | — |

Plasma samples (20 each) from renal cell carcinoma (RCC) patients and normal individuals were purchased from a commercial vendor for initial screening as a potential surrogate tissue. Sample details are summarized in Table 5.

TABLE 5

Plasma samples from renal cell carcinoma (RCC) and normal subjects.

| RCC Samples | | | | | Control Samples | |
|---|---|---|---|---|---|---|
| Gender | Age | Meds | Stage | SubType | Gender | Age |
| Male | 87 | None | 1 | Papillary | Female | 67 |
| Male | 70 | None | 2 | Clear Cell | Male | 63 |
| Male | 87 | None | 2 | Papillary | Male | 62 |
| Male | 74 | Sunitinib | 4 | Clear Cell | Male | 62 |
| Female | 64 | None | 2 | Clear Cell | Male | 65 |
| Male | 67 | Sunitinib | 4 | Clear Cell | Male | 63 |
| Male | 74 | Sunitinib | 4 | Clear Cell | Male | 61 |
| Male | 69 | None | 3 | Clear Cell | Female | 62 |
| Male | 66 | Sunitinib | 4 | Clear Cell | Female | 61 |
| Male | 74 | Sunitinib | 4 | Clear Cell | Male | 63 |
| Female | 87 | None | 2 | Clear Cell | Male | 61 |
| Male | 70 | Sunitinib | 4 | Clear Cell | Male | 66 |
| Male | 69 | Sunitinib | 4 | Clear Cell | Male | 64 |
| Female | 69 | None | 2 | Papillary | Male | 62 |
| Male | 85 | Sorafenib | 3 | Clear Cell | Female | 74 |
| Female | 63 | None | 2 | Papillary | Male | 74 |
| Female | 69 | None | 1 | Papillary | Male | 66 |
| Male | 77 | None | 4 | Clear Cell | Male | 74 |
| Male | 66 | None | 2 | Clear Cell | Male | 61 |
| Male | 72 | None | 3 | Papillary | Female | 65 |

Multiplex immunoassay kits were used for detection of total and/or phosphorylated biomarkers (supplied by Meso Scale Discovery, a division of Meso Scale Diagnostics, LLC, Rockville, Md.). Levels of each biomarker were determined by calibration of the assays with were either purified calibrator proteins or using control cell lysates from appropriately treated cultured cell lines (e.g., cells subjected to conditions known to induce or reduce levels of a specific biomarker). Calibration curves were derived by testing serial dilutions of the calibrator lysates or purified proteins. Levels of biomarkers in test samples were back-calculated from the calibration curves and were expressed in terms of wt. (or arbitrary Units for phospho-protein markers) of protein per weight of tissue extract (for purified calibrators) or in terms of weight of crude control lysate protein per well (for lysate calibrators). Titrations of tumor extracts were carried out to determine the linearity of the assay response to sample dilution and to select the sample dilution that would be appropriate to use for each assay panel.

In general, the assay format was as follows, with minor alterations for specific assay panels as indicated in the assay protocols provided with each assay kit (supplied by Meso Scale Discovery, Rockville, Md.): (1) block MSD MULTI-SPOT® plate for 1 hour with appropriate MSD® blocking solution and wash; (2) add 25 µl assay diluent to each well, if specified; (3) add 25 µl calibrator, or sample (diluted as appropriate) to each well; (4) incubate with shaking for 1-3 hours (time as specified) and wash the well; (5) add 25 µl labeled detection antibody solution to each well; (6) incubate with shaking for 1-2 hours (time as specified) and wash the well; (7) add 150 µl MSD read buffer to each well; (8) read plate immediately on MSD SECTOR® Imager 6000 Reader (supplied by Meso Scale Discovery, Rockville, Md.).

Tumor tissue extracts were assayed at 5-10 µg/well total protein per well. Samples from each set were assayed on the same plate. Measured concentrations for samples from individual mice within a treatment group tended to vary significantly as reflected in the Standard Deviation values shown in the summary below. The signals obtained are not normalized to any housekeeping tissue factor, which may serve to improve animal-to-animal reproducibility, but are normalized to total lysate protein.

| | | SET 1 | | | | | | |
|---|---|---|---|---|---|---|---|---|
| | | CONTROL A375 | | A375 GSK3β shRNA | | A375 shRNA + Dox | | SET 2 SKMEL5 wt | |
| Biomarker | Drug | − | + | − | + | − | + | − | + |
| c-Met (ng/ug pr) | Mean | 0.20 | 0.23 | 0.08 | 0.16 | 0.12 | 0.10 | 0.68 | 0.51 |
| | SD | 0.09 | 0.19 | 0.05 | 0.16 | 0.04 | 0.05 | 0.12 | 0.12 |
| phospho-cMet (pg lys cal/ug pr) | Mean | 2.1 | 3.6 | 1.9 | 1.8 | 2.3 | 1.4 | 5.8 | 15.7 |
| | SD | 1.0 | 2.4 | 0.5 | 2.0 | 1.3 | 0.5 | 1.2 | 21.2 |
| Akt (pg/ug pr) | Mean | 5.2 | 5.3 | 2.2 | 2.2 | 1.6 | 1.6 | 50.0 | 22.3 |
| | SD | 2.6 | 3.0 | 0.3 | 0.8 | 1.6 | 0.8 | 12.8 | 4.1 |
| phosphor-Akt (Units/ug pr) | Mean | 6.9 | 8.5 | 1.9 | 5.9 | 3.3 | 6.1 | 19.6 | 20.5 |
| | SD | 2.8 | 6.8 | 0.4 | 4.7 | 0.8 | 1.7 | 3.6 | 6.8 |
| Rb (pg/ug pr) | Mean | 0.80 | 3.45 | 0.43 | 0.96 | 1.06 | 0.27 | 0.49 | 0.23 |
| | SD | 1.19 | 1.96 | 0.74 | 1.92 | 2.38 | 0.42 | 0.44 | 0.36 |
| phospho-Rb (Units/ug pr) | Mean | 0.15 | 0.21 | 0.05 | 0.13 | 0.10 | 0.10 | 0.54 | 0.62 |
| | SD | 0.08 | 0.16 | 0.02 | 0.16 | 0.05 | 0.04 | 0.20 | 0.26 |

-continued

| | | | | | | | | | |
|---|---|---|---|---|---|---|---|---|---|
| GSK3β (pg/ug pr) | Mean | 114 | 84 | 54 | 50 | 52 | 24 | 139 | 162 |
| | SD | 62 | 56 | 50 | 32 | 13 | 11 | 31 | 48 |
| phospho-GSK3β (Units/ug pr) | Mean | 16.6 | 18.8 | 2.1 | 11.1 | 5.3 | 6.6 | 20.8 | 44.0 |
| | SD | 9.1 | 14.0 | 0.2 | 8.9 | 2.0 | 2.3 | 15.0 | 26.8 |
| β-catenin (pg/ug pr) | Mean | 37 | 32 | 17 | 16 | 36 | 21 | 39 | 31 |
| | SD | 18 | 23 | 2 | 12 | 19 | 13 | 8 | 12 |
| dephospho β-catenin (Units/ug pr) | Mean | 8.4 | 7.3 | 4.6 | 3.0 | 7.3 | 2.9 | 13.1 | 7.4 |
| | SD | 5.4 | 6.3 | 5.5 | 2.7 | 5.2 | 2.2 | 1.4 | 2.5 |
| SRFP-1 (pg/ug pr) | Mean | 1.11 | 1.30 | 0.73 | 0.35 | 0.60 | 0.22 | 0.07 | 0.08 |
| | SD | 0.73 | 0.72 | 0.64 | 0.12 | 0.33 | 0.08 | 0.02 | 0.02 |
| Wnt3A (pg/ug pr) | Mean | 15.3 | 23.2 | 9.3 | 12.0 | 14.4 | 10.4 | 10.4 | 6.2 |
| | SD | 4.1 | 9.2 | 0.9 | 3.6 | 3.9 | 1.9 | 7.7 | 3.7 |
| VEGF (pg/ug pr) | Mean | 1.8 | 10.8 | 1.7 | 8.5 | 1.8 | 2.6 | 0.4 | 0.8 |
| | SD | 0.69 | 9.40 | 0.92 | 2.77 | 0.84 | 1.08 | 0.03 | 0.40 |
| E-Cadherin (pg/ug pr) | Mean | ND | ND | ND | ND | ND | ND | 11.2 | 10.9 |
| | SD | — | — | — | — | — | — | 5.65 | 5.15 |

| | | SET 2 SKMEL5 GSK3β+ | | SET 3 | | | |
|---|---|---|---|---|---|---|---|
| | | | | A498 | | 786-0 | |
| Biomarker | Drug | − | + | − | + | − | + |
| c-Met (ng/ug pr) | Mean | 0.53 | 0.59 | 0.75 | 1.47 | 1.12 | 1.26 |
| | SD | 0.11 | 0.40 | 0.80 | 0.73 | 0.62 | 1.08 |
| phospho-cMet (pg lys cal/ug pr) | Mean | 6.1 | 7.2 | 106.7 | 73.6 | 22.3 | 31.5 |
| | SD | 1.4 | 5.0 | 168.0 | 42.0 | 12.5 | 16.4 |
| Akt (pg/ug pr) | Mean | 31.8 | 32.4 | 4.1 | 6.3 | 17.5 | 9.3 |
| | SD | 18.2 | 16.8 | 3.8 | 4.7 | 12.2 | 9.4 |
| phosphor-Akt (Units/ug pr) | Mean | 19.4 | 14.3 | 47.0 | 59.1 | 75.4 | 78.5 |
| | SD | 8.4 | 9.1 | 32.0 | 36.2 | 56.0 | 38.9 |
| Rb (pg/ug pr) | Mean | 0.75 | 0.63 | 0.00 | 0.00 | 2.47 | 6.48 |
| | SD | 0.79 | 0.56 | 0.00 | 0.00 | 3.64 | 9.89 |
| phospho-Rb (Units/ug pr) | Mean | 0.45 | 0.53 | 0.02 | 0.08 | 0.14 | 0.14 |
| | SD | 0.12 | 0.34 | 0.03 | 0.05 | 0.08 | 0.14 |
| GSK3β (pg/ug pr) | Mean | 97 | 88 | 18 | 24 | 71 | 61 |
| | SD | 29 | 31 | 12 | 13 | 43 | 15 |
| phospho-GSK3β (Units/ug pr) | Mean | 10.0 | 7.9 | 2.4 | 14.2 | 4.4 | 5.9 |
| | SD | 5.2 | 3.2 | 0.9 | 8.2 | 2.9 | 4.5 |
| β-catenin (pg/ug pr) | Mean | 35 | 39 | 20 | 34 | 86 | 82 |
| | SD | 12 | 22 | 14 | 22 | 44 | 34 |
| dephospho β-catenin (Units/ug pr) | Mean | 13.6 | 12.6 | 1.8 | 3.4 | 20.2 | 23.3 |
| | SD | 3.2 | 9.3 | 1.6 | 2.5 | 12.4 | 13.1 |
| SRFP-1 (pg/ug pr) | Mean | 0.13 | 0.22 | 0.09 | 0.15 | 0.17 | 0.23 |
| | SD | 0.03 | 0.04 | 0.08 | 0.04 | 0.04 | 0.03 |
| Wnt3A (pg/ug pr) | Mean | 14.3 | 11.4 | 12.7 | 8.8 | 15.6 | 11.8 |
| | SD | 15.6 | 6.3 | 7.4 | 3.4 | 2.9 | 3.0 |
| VEGF (pg/ug pr) | Mean | 1.1 | 7.2 | 2.1 | 5.8 | 8.5 | 38.3 |
| | SD | 1.33 | 6.35 | 0.73 | 3.35 | 8.93 | 4.86 |
| E-Cadherin (pg/ug pr) | Mean | 0.0 | 0.0 | 0.1 | 0.0 | 0.2 | 0.1 |
| | SD | 0.02 | 0.03 | 0.05 | 0.00 | 0.07 | 0.04 |

Levels of individual markers in tumor sample sets 1, 2, and 3 measured on MSD panels are shown in FIG. 1(*a*)-(*n*). Samples that were not treated with drug are designated as (−) and those treated with drug as (+). The A375 and SKMEL5 tumor-bearing mice were treated with sorafenib, and the A498 and 786-0 tumor-bearing mice treated with sunitinib.

Figure 2:
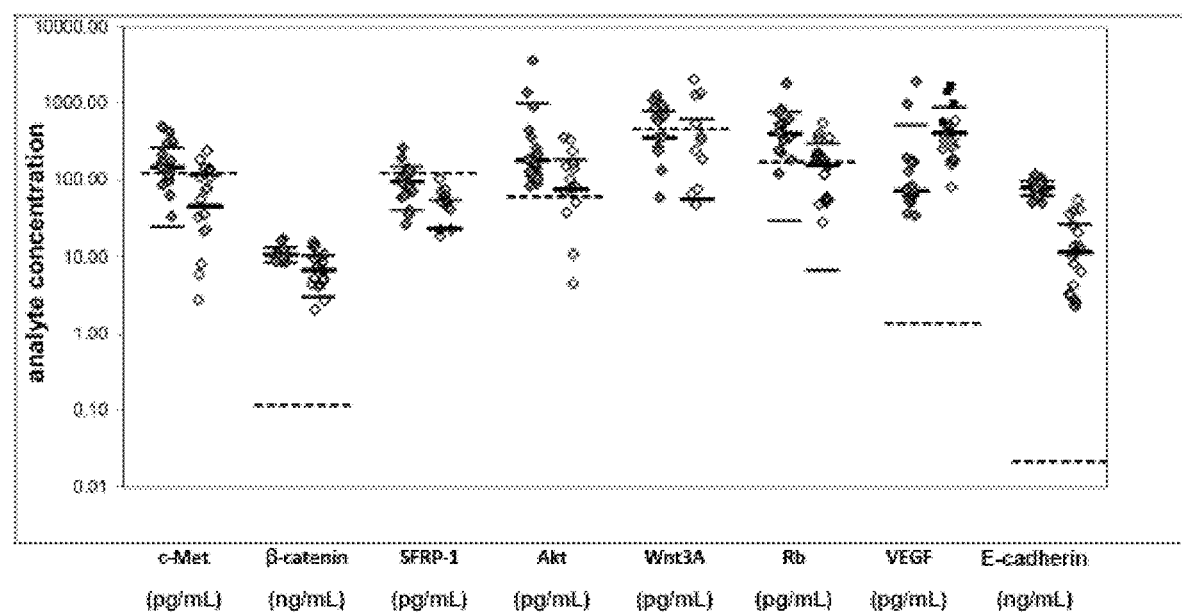
FIG. 2 shows the measured levels of selected analytes in plasma samples from control (✳) and renal cell carcinoma patients (◇). VEGF levels for patients who had received sunitinib (n=7, ■) or sorafenib (n=1, ✳) are indicated. Sample concentration medians (▬), 1 standard deviation above or below the medians (∿∿∿), as well as assay detection limits are shown (— — —).

Some of the evaluated markers are expected to be secreted and hence found in culture media and potentially in plasma. Evaluations of culture media showed detectable levels of c-Met to be shed from cells (data not shown), but minimal or no detectable Wnt3A, or SFRP-1 were measured. Plasma samples from RCC patients and normal individuals were also evaluated and the data are summarized in Table 7 and FIG. 2.

TABLE 7

Measured analyte concentrations in RCC (n = 20) and control (n = 20) patient samples.

| | | c-Met pg/mL | b-catenin ng/mL | SFRP-1 pg/mL | Akt pg/mL | Wnt3A pg/mL | Rb pg/mL | VEGF pg/mL | E-cadherin ng/mL |
|---|---|---|---|---|---|---|---|---|---|
| Control | Min | 34 | 9 | 26 | 84 | 0 | 0 | 35 | 50 |
| | Mean | 185 | 11 | 103 | 448 | 469 | 463 | 226 | 79 |
| | Median | 144 | 11 | 95 | 179 | 354 | 403 | 73 | 80 |

TABLE 7-continued

Measured analyte concentrations in RCC (n = 20) and control (n = 20) patient samples.

| | | c-Met pg/mL | b-catenin ng/mL | SFRP-1 pg/mL | Akt pg/mL | Wnt3A pg/mL | Rb pg/mL | VEGF pg/mL | E-cadherin ng/mL |
|---|---|---|---|---|---|---|---|---|---|
| | Max | 485 | 17 | 255 | 3,625 | 1,283 | 1,797 | 1,915 | 116 |
| | St Dev | 119 | 2 | 54 | 812 | 429 | 373 | 446 | 17 |
| RCC | Min | 0 | 2 | 0 | 0 | 0 | 0 | 79 | 2 |
| | Mean | 69 | 7 | 31 | 99 | 325 | 169 | 558 | 16 |
| | Median | 46 | 7 | 23 | 76 | 57 | 154 | 403 | 11 |
| | Max | 240 | 16 | 105 | 354 | 2,057 | 551 | 1,671 | 55 |
| | St Dev | 70 | 4 | 32 | 109 | 568 | 148 | 477 | 15 |
| Detection limit | | 124 | 0.116 | 122 | 61 | 461 | 173 | 1.35 | 0.022 |

The two drugs evaluated in the studies described herein, sorafenib and sunitinib, have anti-angiogenesis and anti-tumor growth effects in xenograft models and in clinical tests for multiple cancer types, and have been used for treatment of a number of cancers. Metastatic RCC tumors and melanoma are hard to treat and sunitinib and sorafenib are among the few VEGF-targeting therapies that have demonstrated clinical utility. Both drugs are small molecule inhibitors that target multiple kinases and have effects on the vascularization of the tumors. Major targets for sorafenib include the Ras/Raf/MEK/ERK and receptors such as VEGFR, PDGFR, and c-Kit. The Raf kinase pathway is activated in a number of solid tumors and sorafenib treatments have been found to be effective in RCC and melanoma tumors. Inhibition of the Raf/Mek/Erk pathway in endothelial cells may be the main way in which the anti-angiogenic activity of sorafenib occurs (Murphy et al. 2006). Sunitinib, like sorafenib, targets the VEGF receptors and other receptor tyrosine kinases, but unlike sorafenib does not affect Raf signaling.

The Wnt/β-catenin and HGF/c-Met signaling pathways play significant roles is several tumor types, including RCC and melanoma. Melanoma and RCC xenografts were used in this study, including tumor cells transfected to modulate their GSK3β activities, and then treated with/without sunitinib or sorafenib. The effects on various biomarkers are summarized below:

VEGF: Sorafenib and sunitinib treatment of 786-0 cells resulted in increased levels of VEGF. RCC patient plasma VEGF levels were found to be higher than for control plasma. Furthermore, significantly higher levels of VEGF were observed in plasma of RCC patients who had received sunitinib treatment. These data support the use of plasma VEGF as an indicator of sorafenib and sunitinib responsiveness, hence support use of plasma as a potential surrogate tissue for this marker.

Akt: The 786-0 tumors and SKMEL5 tumors responded to sunitinib or sorafenib treatments, respectively, with reduced levels of total Akt, and unchanged phospho-Akt levels, with a net effect of increased relative phospho-Akt levels.

GSK3β activity: Two of the cell systems selected have defined basal activities of GSK3β (high in A375 and low in SKMEL5) and were transfected to express either a constitutively active form of GSK3β (in SKMEL5 cells), or an shRNA to down-modulate GSK3β expression (in A375 cells). SKMEL5 melanoma cells have a B-raf mutation, a common mutation in this cancer type, and these cells also have constitutively low GSK3β activity. The levels of total GSK3β were high in wild type SKMEL5 and A375 melanoma tumors and decreased with GSK3β shRNA in A375 tissues, but also with expression of active GSK3β in SKMEL5 tissues (which can indicate increased turnover). Phospho-GSK3β levels were highest in control SKMEL5 and A375 cells, and significantly lower in the tissues expressing active GSK3β and GSK3β shRNA, respectively.

Active (dephospho) β-catenin was decreased with sorafenib treatment of the wt SMKEL5 tumors. A reduction in GSK3β phosphorylation was not observed, but the assays were designed to measure total cellular protein, and any changes in subcellular fractions of the protein, such as the mitochondrial GSK3β, may not be distinguished in the assays conducted.

The wild type A375 tumors showed no changes with sorafenib treatment for either total or phospho-GSK3β. However, in the shRNA transfected A375 tumors, sorafenib treatment caused a reduction in levels of active β-catenin, as seen in the wild type SKMEL5 tumors. The wild type A375 cells are reported to exhibit resistance to sorafenib-induced apoptosis due to pro-survival effects of endogenous active GSK3β, and down-modulation of GSK3β with shRNA shown to increase sorafenib-induced apoptosis (Panka et al. 2008). Thus, changes in levels of dephospho-β-catenin may be indicative of susceptibility of the tumors to sorafenib-induced apoptosis.

GSK3β effect on E-cadherin: The most dramatic change observed was the high level of E-cadherin (a tumor suppressor protein) expressed in the wild type SKMEL5 cells and its reduction over 500-fold with expression of active GSK3β. E-cadherin functions at the adherens junctions to enhance cell-cell contacts. The loss of E-cadherin is predicted to make a tumor more metastatic (Onder et al. 2008), promoting tumorigenesis by releasing membrane bound β-catenin into the cytosol, and stimulating canonical Wnt signaling (Prasad et al. 2009). Generally, loss of GSK3β activity is seen as the trigger of Wnt signaling activation, and correlated E-cadherin loss. Loss of GSK3β activity is supposed to have an inhibitory effect on E-cadherin expression by upregulating the E-cadherin transcriptional repressors Snail and Slug. Inactivation of GSK3β increases the expression of Snail (Zhou et al. 2004) and stabilization of Slug (Ye et al. 2010). GSK3β inhibition has also been shown to lead to increased activity of NFκB (Rao et al. 2004). NFκB induces expression of Slug and Snail, which repress E-cadherin expression (Baranwal and Alahari 2009), and loss of E-cadherin leads to increased activity of NFκB in malignant melanoma (Kuphal et al. 2004).

Increased GSK3β activity was found to lead to E-cadherin down-regulation, contrary to expectations based on these literature reports. The SKMEL5 cells, which had low GSK3β activity, had high E-cadherin expression, and expression of active GSK3β abolished E-cadherin expression. Treatment of the SKMEL5 cells, transfected or not, with sorafenib had no additional effect on levels of E-cadherin. In the A498 and 786-0 cells, the levels of E-cadherin were much lower than in the SKMEL5 cells, and decreased further with sunitinib treatment, which, at least in the A498 cells, correlated with an increased level of inactive phospho-GSK3β. No detectable levels of E-cadherin were observed in the A375 tissues, a highly malignant cell line.

E-Cadherin levels in patient plasma: Plasma levels of soluble E-cadherin in RCC patients were significantly lower than observed for control individual samples.

Wnt3A and SFRP-1: Wnt3A, SFRP-1, and VEGF are all secreted proteins, but their levels are detectable in cells to differing extents, with Wnt3A and SFRP-1 close to detection limits for most samples, and VEGF levels easily detectable in all cases. The Wnt3A and SFRP-1 levels were highest in the A375 cells and decreased with expression of GSK3β shRNA. There was an increase in levels of SFRP-1 with expression of active GSK3β in the SKMEL5 cells. SFRP-1 levels appeared to increase in transfected SKMEL5 cells (active GSK3β), not wild type, and to decrease in transfected A375 cells (inactive GSK3β) versus wild type. Changes in SFRP levels may reflect changes in GSK3β activity.

c-Met: The A498 and 786-0 RCC tumors are both VHL-null, hence have deregulated Wnt signaling. The 786-0 cells had relatively high levels of the downstream target β-catenin and active dephospho-β-catenin, while levels in the A498 cells were relatively low. Both tumors also had higher levels of c-Met and phospho-c-Met than did the melanoma tumors.

Rb: It has been suggested that the Rb/E2F pathway suppresses the Wnt signaling pathway (Wu et al. 2011). Phospho-Rb was measured in all samples in the current study, and SKMEL5 cells expressed 5 to 20-fold higher levels than the other tumor types. No clear effect of drug treatment was seen in all cases. The total Rb levels measured at or below the detection limits in most samples, but there appeared to be an increase in its levels in control A375 cells with sorafenib treatment.

Various publications and test methods are cited herein, the disclosures of which are incorporated herein by reference in their entireties, In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

REFERENCES

Bachelder R E, Crago A, Chung J, Wendt M A, Shaw L M, Robinson G, Mercurio A M. (2001) Vascular endothelial growth factor is an autocrine survival factor for neuropilin-expressing breast carcinoma cells. Cancer Res. 1; 61(15):5736-40.

Chang Y S, Adnane J, Trail P A, Levy J, Henderson A, Xue D, Bortolon E, Ichetovkin M, Chen C, McNabola A, Wilkie D, Carter C A, Taylor I C, Lynch M, Wilhelm S. (2007) Sorafenib (BAY 43-9006) inhibits tumor growth and vascularization and induces tumor apoptosis and hypoxia in RCC xenograft models. Cancer Chemother. Pharmacol. 59(5):561-74.

Chen Z, Trotman L C, Shaffer D, Lin H K, Dotan Z A, Niki M, Koutcher J A, Scher H I, Ludwig T, Gerald W, Cordon-Cardo C, Pandolfi P P. (2005) Crucial role of p53-dependent cellular senescence in suppression of Pten-deficient tumorigenesis. Nature 436(7051):725-30.

Fan Y, Borowsky A D, Weiss R H. (2003) An antisense oligodeoxynucleotide to p21(Waf1/Cip1) causes apoptosis in human breast cancer cells. Mol Cancer Ther. 2(8): 773-82.

Garcia J A, Rini B I. (2007) Recent progress in the management of advanced renal cell carcinoma. CA Cancer J. Clin. March-April; 57(2):112-25.

Horiguchi A, Oya M, Uchida A, Marumo K, Murai M. (2003) Elevated Akt activation and its impact on clinicopathological features of renal cell carcinoma. J. Urol. 169(2):710-13.

Jung J E, Lee H G, Cho I H, Chung D H, Yoon S H, Yang Y M, Lee J W, Choi S, Park J W, Ye S K, Chung M H. (2005) STAT3 is a potential modulator of HIF-1-mediated VEGF expression in human renal carcinoma cells. FASEB J. 19(10):1296-8.

Kummar S, Kinders R, Rubinstein L, Parchment R E, Murgo A J, Collins J, Pickeral O, Low J, Steinberg S M, Gutierrez M, Yang S, Helman L, Wiltrout R, Tomaszewski J E, Doroshow J H. (2007) Compressing drug development timelines in oncology using phase '0' trials. Nat Rev Cancer. 7(2):131-39.

Lee T H, Seng S, Sekine M, Hinton C, Fu Y, Avraham H K, Avraham S. (2007) Vascular endothelial growth factor mediates intracrine survival in human breast carcinoma cells through internally expressed VEGFR1/FLT1. PLoS Med. 4(6):e186.

Li Y, Dowbenko D, Lasky L A. (2002) AKT/PKB phosphorylation of p21Cip/WAF1 enhances protein stability of p21Cip/WAF1 and promotes cell survival. J Biol Chem. 277(13):11352-61.

Masood R, Cai J, Zheng T, Smith D L, Hinton D R, Gill P S. (2001) Vascular endothelial growth factor (VEGF) is an autocrine growth factor for VEGF receptor-positive human tumors. Blood. 98(6):1904-13.

Miyata Y, Kanetake H, Kanda S. (2006) Presence of phosphorylated hepatocyte growth factor receptor/c-Met is associated with tumor progression and survival in patients with conventional renal cell carcinoma. Clin Cancer Res. 12(16):4876-81.

Motoshima H, Goldstein B J, Igata M, Araki E. J. (2006) AMPK and cell proliferation-AMPK as a therapeutic target for atherosclerosis and cancer. Physiol. 574(Pt 1):63-71.

Murphy D A, Makonnen S, Lassoued W, Feldman M D, Carter C, Lee W M. (2006) Inhibition of tumor endothelial ERK activation, angiogenesis, and tumor growth by sorafenib (BAY43-9006). Am J Pathol. 169(5):1875-85.

Nagata D, Mogi M, Walsh K. (2003) AMP-activated protein kinase (AMPK) signaling in endothelial cells is essential for angiogenesis in response to hypoxic stress. J Biol Chem. 278(33):31000-6.

Panka D J, Cho D C, Atkins M B, Mier J W. (2008) GSK-3beta inhibition enhances sorafenib-induced apoptosis in melanoma cell lines. J Biol Chem. 283(2):726-32.

Rini B I. (2007) Vascular endothelial growth factor-targeted therapy in renal cell carcinoma: current status and future directions. Clin Cancer Res. 13(4):1098-106.

Waltenberger J, Claesson-Welsh L, Siegbahn A, Shibuya M, Heldin C H. (1994) Different signal transduction properties of KDR and Flt1, two receptors for vascular endothelial growth factor. J Biol Chem. 269(43):26988-95.

Weiss R H (2003) p21Waf1/Cip1 as a therapeutic target in breast and other cancers. Cancer Cell. 4(6):425-9.

Weiss R H, Borowsky A D, Seligson D, Lin P Y, Dillard-Telm L, Belldegrun A S, Figlin R A, Pantuck A D. (2007) p21 is a prognostic marker for renal cell carcinoma:

implications for novel therapeutic approaches. J Urol. 177(1):63-8; discussion 68-9.

Wilhelm S M, Carter C, Tang L, Wilkie D, McNabola A, Rong H, Chen C, Zhang X, Vincent P, McHugh M, Cao Y, Shujath J, Gawlak S, Eveleigh D, Rowley B, Liu L, Adnane L, Lynch M, Auclair D, Taylor I, Gedrich R, Voznesensky A, Riedl B, Post L E, Bollag G, Trail P A. (2004) BAY 43-9006 exhibits broad spectrum oral antitumor activity and targets the RAF/MEK/ERK pathway and receptor tyrosine kinases involved in tumor progression and angiogenesis. Cancer Res. 64(19):7099-109.

The invention claimed is:

1. A method of administering a treatment regimen to a patient in need thereof for treating renal cell carcinoma (RCC), wherein said treatment regimen is sunitinib, said method comprising:
   (a) measuring a baseline level of at least one biomarker in a test sample obtained from said patient before undergoing said treatment regimen, wherein the at least one biomarker is SFRP-1 and measuring an interim level of the at least one biomarker in a test sample obtained from the patient after undergoing said treatment regimen;
   (b) comparing said baseline level of said at least one biomarker to the interim level of said at least one biomarker; and
   (c) continuing administration of said treatment regimen to said patient when in step (b) said interim level of SFRP-1 is higher than the baseline level.

2. The method according to claim 1, wherein said at least one biomarker is a plurality of biomarkers including SFRP-1, and wherein said measuring step comprises conducting a multiplexed assay measurement of said plurality of biomarkers in said test sample, wherein said multiplexed assay measurement is conducted using one reaction volume comprising said test sample.

3. The method of claim 1 wherein said method comprises measuring levels of two or more biomarkers.

4. The method of claim 1 wherein said treatment regimen comprises administering an agonist of a VEGF- signaling pathway.

5. The method of claim 1, which comprises an immunoassay.

6. The method of claim 5, which is conducted in a multi-well assay plate.

7. The method of claim 6, wherein the multi-well assay plate comprises a plurality of electrodes.

8. The method of claim 5, which is conducted in a cartridge.

9. The method of claim 8, wherein the cartridge comprises a plurality of electrodes.

10. The method of claim 5, wherein the immunoassay comprises a support comprising a binding reagent immobilized thereto, wherein said first binding reagent binds at least one of said biomarkers, wherein said support is a particle.

11. The method of claim 5, wherein the immunoassay further comprises a detectable label to measure the level of said biomarker.

12. The method of claim 11, wherein the detectable label is measured by a measurement of light scattering, optical absorbance, fluorescence, chemiluminescence, electrochemiluminescence, bioluminescence, phosphorescence, radioactivity, magnetic field, or combinations thereof.

13. The method of claim 11, wherein the detectable label is an ECL label and the measuring step comprises measuring an ECL signal.

* * * * *